United States Patent
Webster et al.

(10) Patent No.: US 10,231,864 B1
(45) Date of Patent: Mar. 19, 2019

(54) SLEEP APNEA THERAPY DEVICE THAT AUTOMATICALLY ADJUSTS THE FRACTION OF INSPIRED CARBON DIOXIDE

(71) Applicant: ComfortApnea LLC, Madison, WI (US)

(72) Inventors: John Webster, Madison, WI (US); Icaro dos Santos, Waunakee, WI (US); Jacob Levin, Verona, WI (US); Mehdi Shokoueinejad, Madison, WI (US); Fa Wang, Madison, WI (US); Jerome Dempsey, Madison, WI (US); Ailiang Xie, Madison, WI (US)

(73) Assignee: John Webster, Madison, WI (US)

( * ) Notice: Subject to any disclaimer, the term of this patent is extended or adjusted under 35 U.S.C. 154(b) by 0 days.

(21) Appl. No.: 15/376,180

(22) Filed: Dec. 12, 2016

Related U.S. Application Data

(60) Provisional application No. 62/266,037, filed on Dec. 11, 2015.

(51) Int. Cl.

| | | |
|---|---|---|
| *A61M 16/12* | (2006.01) | |
| *A61B 5/1455* | (2006.01) | |
| *A61B 5/00* | (2006.01) | |
| *A61M 16/00* | (2006.01) | |
| *A61M 16/06* | (2006.01) | |

(Continued)

(52) U.S. Cl.
CPC .......... *A61F 5/566* (2013.01); *A61B 5/14552* (2013.01); *A61B 5/4818* (2013.01); *A61M 16/0045* (2013.01); *A61M 16/0075* (2013.01); *A61M 16/0078* (2013.01); *A61M 16/0488* (2013.01); *A61M 16/0622* (2014.02); *A61M 16/0666* (2013.01); *A61M 16/122* (2014.02); *A61M 2016/003* (2013.01); *A61M 2202/0225* (2013.01); *A61M 2205/3303* (2013.01); *A61M 2205/3306* (2013.01); *A61M 2205/3368* (2013.01); *A61M 2205/3375* (2013.01); *A61M 2205/3576* (2013.01); *A61M 2205/50* (2013.01); *A61M 2230/432* (2013.01)

(58) Field of Classification Search
CPC ........ A61M 16/0045; A61M 2016/103; A61M 16/0081; A61M 16/0605; A63B 23/18
See application file for complete search history.

(56) References Cited

U.S. PATENT DOCUMENTS

| | | | | |
|---|---|---|---|---|
| 5,647,345 A | * | 7/1997 | Saul .................. | A61M 16/0045 128/200.24 |
| 6,012,455 A | * | 1/2000 | Goldstein ......... | A61M 16/0488 128/204.18 |

(Continued)

OTHER PUBLICATIONS

Khayat (Cardiorespiratory Effects of Added Dead Space in Patients with Heart Failure and Central Sleep. Chest 123; 1551-1560, 2003).*

(Continued)

*Primary Examiner* — Peter S Vasat
(74) *Attorney, Agent, or Firm* — Boardman & Clark LLP

(57) ABSTRACT

A comfortable device for treating sleep apnea incorporates a mask, a flexible hose and a chamber for collecting expired air containing $CO_2$. A sensor detects apnea and a control system automatically adjusts the amount of rebreathed $CO_2$ to minimize apnea and also minimize arousal.

23 Claims, 16 Drawing Sheets

(51) Int. Cl.
*A61F 5/56* (2006.01)
*A61M 16/04* (2006.01)

(56) References Cited

U.S. PATENT DOCUMENTS

| | | | | |
|---|---|---|---|---|
| 6,165,105 | A * | 12/2000 | Boutellier | A63B 23/18 128/204.22 |
| 7,886,740 | B2 | 2/2011 | Thomas et al. | |
| 2008/0302364 | A1* | 12/2008 | Garde | A61M 16/0045 128/204.23 |
| 2011/0288428 | A1* | 11/2011 | Valentine | A61B 5/097 600/529 |
| 2014/0283831 | A1* | 9/2014 | Foote | A61M 16/026 128/204.19 |

OTHER PUBLICATIONS

Antic, NA et al., "A Randomized Controlled Trial of Nurse-Led Care for Symptomatic Moderate-Severe Obstructive Sleep Apnea", Am. J Respir. Crit. Care Med., Mar. 15, 2009; 179 (8):501-8.
Ayas, NT et al., "Cost-Effectiveness of Continuous Positive Airway Pressure Therapy for Moderate to Severe Obstructive Sleep Apnea/Hypopnea", Arch, Intern. Med., May 8, 2006 166(9):977-84.
Bearpark, H. et al., "Snoring and Sleep Apnea. A population study in Australian men.", Am. J. Respir. Crit. Care Med., May 1995; 151 (5):1459-65.
Behar, J. et al., "A Review of Current Sleep Screening Applications for Smartphones", Physiological Measurement; 2013; 34 R29-46.
Berssenbrugge, A. et al., "Mechanisrna of Hypoxia-Induced Periodic Breathing During Sleep in Humans", J. Physiol.; Oct. 1983; 343: 507-24.
Bixler, EO et al., "Prevalence of Sleep-Disordered Breathing in Women: Effects of Gender", Am. J. Respir. Care Med.. Mar. 2001; 163 (3 Pt1):608-13.
Collop, N. , "The Effect of Obstructive Sleep Apnea on Chronic Medical Disorders", Cleveland Clinic Journal of Medicine, 2007, 74 72-8.
Cowie, MR et al., "Adaptive Servo-Ventilation for Central Sleep Apnea in Systolic Heart Failure", New England Journal of Medicine: Sep. 1, 2015.
Dempsey, JA et al., "Pathophysiology of Sleep Apnea", Physiol. Rev.; Jan. 2010;90(1):47-112. doi: 10.1152/physrev.00043.2008. Review. Erratum in: Physiol. Rev. Apr. 2010; 90 (2)797-8.
Dempsey, JA et al., "Physiology in Medicine: Obstructive Sleep Apnea athogenesis and Treatment—Considerations Beyond Airway Anatomy", J. Appl. Physiol. (1985); Jan. 1, 2014; 116 (1):3-12.
Deutsch, PA et al., "Cost-Effectiveness of Split-Night Polysomnography and Home Studies in the Evaluation of Obstructive Sleep Apnea Syndrome", Journal of Clinical Sleep Medicine; JCSM; Official publication of the American Academy of Sleep Medicine, 2006, 2, 145-53.
Findley, LJ et al., "Automobile Accidents Involving Patients with Obstructive Sleep Apnea", The American Review of Repiratory Disease, 1988, 138 337-40.
Flemons, WW et al., "Home Diagnosis of Sleep Apnea: A Systematic Review of the Literature", An evidence review co-sponsored by the American Academy of Sleep Medicine, the American College of Chest Physicians, and the American Thoracic Society, Chest 2003, 124 1543-79.
Giannoni, A. et al., "Real-time Dynamic Carbon Dioxide Administration: A Novel Treatment Strategy for Stabilization of Periodic Breathing with Potential Application to Central Sleep Apnea", J. Am. Coll. Cardiol., 2010, 56 1832-7.
Guilleminault, C. et al., "Obstructive Sleep Apnea", Current Treatment Options in Neurology; 2004; 6 309-17.
Hillman, DR et al,, "The Economic Cost of Sleep Disorders", Sleep; 2006; vol. 29, No, 3, 299-305.
Hossain, JL, et al., "The Prevalence, Cost Implications, and Management of Sleep Disorders: An Overview", Sleep & Breathing= Schlaf & Atmung, 2002, 6 85-102.
Ip, MS et al., "A Community Study of Sleep-Disordered Breathing in Middle-Aged Chinese Men in Hong Kong", Chest., Jan. 2001; 119 (1):62-9; Chest., Jan. 2001; 125(1):127-34.
Ip, MS et al., "A Community Study of Sleep-Disordered Breathing in Middle-Aged Chinese Women in Hong Kong: Prevalence and Gender Differences", Chest., Jan. 2004; 125 (1):127-34.
Kim, J. et al., "Prevalence of Sleep-Disordered Breathing in Middie-Aged Korean Men and Women", Am. J. Respir. Crit. Care Med., Nov. 15, 2004; 170(10:1108-13. Epub Sep. 3, 2004.
Kryger, MH et al., "Long Term Use of a Nasal Expiratory Positive Airway Pressure (EPAP) Device as a Treatment for Obstructive Sleep Apnea", Sleep Abstract Supplement, 2011 (34):A118.
Leger, D. et al., "Impact of Sleep Apnea on Economics", Sleep Medicine Reviews, 2012, 16 455-62.
Masa, JF et al., "Effectiveness of Home Respiratory Polygraphy for the Diagnosis of Sleep Apnoea and Hypopnoea Syndrome", Thorax., Jul. 2011; 66 (7):567-73. doi: 10.1136/thx.2010.152272. Epub May 20, 2011.
Panossian, LA et al., "Reivew of Sleep Disorders", The Medical Clinics of North America, 2009, 93 407-25 ix.
Richert, AC et al., "A Review of Common Sleep Disorders", CNS Spectr., Feb. 2003; 8 (2)102-9.
Udwadia, ZF et al., "Prevalence of Sleep-Disordered Breathing and Sleep Apnea in Middle-Aged Urban Indian Men", Am. J. Respir. Crit. Care Med., Jan. 15, 2004; 169 (2)168-73; Epub Nov. 6, 2003.
Weaver, TE et al., "Adherence to Continuous Positive Airway Pressure Therapy:The Challenge to Effective Treatment", Proc. Am. Thorac. Soc., Feb. 15, 2008; 5(2):173-8.
Wohlgemuth, WK et al., "Attempters, Adherers, and Non-Adherers: Latent Profile Analysis of CPAP Use With Correlates", Sleep Med., Mar. 2015; 16(3):336-42; doi: 10.1016/j.sleep.2014.08.013. Epub Sep. 17, 2014.
Xie, A. et al., "Effects of Stabilizing or Increasing Respiratory Motor Outputs on Obstrucive Sleep Apnea", J. Appl. Physiol., 2013; 115, 22-23; retrieved from http://jap.physiology.org/content/early/2013/04/15/japplphysiol.00064.2013.
Young, T. et al., "Epidemiology of Obstructive Sleep Apnea: A Population Health Perspective", Am. J. Respir. Crit. Care Med., 2002, 164 1217-39.

* cited by examiner

SLEEP APNEA THERAPY DEVICE THAT AUTOMATICALLY ADJUSTS THE FRACTION OF INSPIRED CARBON DIOXIDE

CROSS-REFERENCE TO RELATED APPLICATIONS

This application claims the benefit of and priority to U.S. Provisional Patent Application, Ser. No. 62/266,037, filed Dec. 11, 2015, entitled SLEEP APNEA THERAPY DEVICE THAT AUTOMATICALLY ADJUSTS THE AMOUNT OF INSPIRED CARBON DIOXIDE, the entire content of which is hereby incorporated by reference herein in its entirety.

FIELD

The inventions described herein relate to systems and devices for the treatment of sleep apnea.

BACKGROUND

Sleep apnea is a common sleeping disorder in which an obstruction of the throat or absence of respiratory response prevents air from entering the lungs. Halted breathing results in increased concentrations of $CO_2$ in the blood stream, resulting in an unconscious, regulatory respiratory response. An escalating 10% of the general US population has clinically significant sleep apnea (Peppard 2013), where breathing stops repeatedly and interrupts sleep, leading to significant cardio-vascular morbidities, insulin resistance, neural injury, and accelerated mortality.

Current therapies for obstructive, central, and complex sleep apnea focus on ameliorating the physiological symptoms of sleep apnea. All currently available therapies attempt to open the soft tissue of the airway, most often through positive airway pressure, and thereby allow stable breathing without subconscious awakening from the rapid eye moment (REM) cycle. There are currently multiple approaches to increase positive airway pressure, including but not limited to Continuous Positive Airway Pressure (CPAP), Adaptive Servo-Ventilation (ASV), and Expiratory Positive Airway Pressure (EPAP).

Other approaches, while less common, include jaw displacement devices, surgery, and even novel pharmaceuticals. While targeting the direct cause of sleep apnea, closing of the throat and neurological "forgetfulness" to breathe, as the primary means to treat apneas, other therapies employ a holistic methodology to treat the associated medical disorders or medication side effects.

The standard therapy for sleep apnea is Continuous Positive Airway Pressure (CPAP). CPAP utilizes a machine that delivers positive air pressure through a facemask during sleep. The air pressure from the mask is greater than the surrounding air, and as a result, the upper airway passages are forced open for the movement of air. Contrary to popular belief, CPAP isn't a ventilator that breathes for the individual; instead it simply keeps the airway open so that the individuals can breathe for themselves. Keeping the airway open also prevents snoring, a major complaint of partners of individuals with sleep apnea. CPAP requires a blower, increased pressure and a tight fitting mask, rendering patients to reject it. CPAP entails the patient wearing a mask over their nose and mouth, through which an air blower blows air through the nasal passages. The pressure is constant and continuous, but can be adjusted during the night using a system which detects air flow limitations and adjusts its CPAP level accordingly.

CPAP has been shown to attenuate Obstructive Sleep Apnea (OSA), improve nocturnal oxygenation levels, and improve the ejection fraction. CPAP is effective when used correctly, but due to side effects, approximately 50% (Wohlgemuth 2014) of patients are intolerant or non-compliant, and even in "compliant" patients usage is usually limited to 4 to 5 hours/night, 5 days/week (Weaver and Grunstein 2008). At this time, CPAP is the most common and reliable treatment; it is considered the "gold standard" of sleep apnea therapy. Despite this, many patients find it uncomfortable and cumbersome, reflective of the noncompliance rate of 50% of patients (Wohlgemuth 2014). Most often patient dissatisfaction comes from the time and patience required in learning to adjust the CPAP mask, and the noisiness of the built-in humidifier. Moreover, as indicated CPAP usage has various side effects, some of which can include skin abrasions, bruising, chafing, nasal congestion or dryness, and abdominal cramping (Guilleminault and Abad 2004; Weaver and Grunstein 2008). Unfortunately, among other concerns, this minimal use of CPAP may not be sufficient to prevent cardiovascular sequelae (Dempsey 2010).

Adaptive Servo-Ventilation (ASV) systems, which are an alternative to CPAP, use advanced algorithms to monitor, predict, and control respiratory gas levels as well as maintain stable breathing patterns. There are three factors that contribute to these advanced algorithms, including: the patient's most recent, average respiratory rate; the instantaneous rate, direction, and change in patient's airflow; and a backup respiratory rate of 15 breaths per minute (meaning the machine will force air into the lungs if breaths aren't taken.) These features allow for minimal support during stable breathing, however, the moment hypopneas or apneas begin to occur, the machine increases air pressure to stabilize breathing. In essence, ASV systems ventilate the patient appropriately during periods of hypopneas or apneas, while reducing support during periods of hyperventilation and normal breathing. Unfortunately, ASV has recently been shown to have serious side effects in Congestive Heart Failure (CHF) patients with central apnea (Cowie 2015).

Expiratory Positive Airway Pressure (EPAP) is the most recent therapy to be approved by the FDA. This therapy utilizes small, single use "plugs" that are placed over each nostril before sleeping. The device permits air to move in freely, however, it increases air pressure in the patient dead space upon exhalation. The theory is that an increase in dead space airway pressure will keep the throat open, thus reducing apneic events. Kryger et al. (2011) describes that over a twelve-month period the number of events per hour was decreased from 15.7 to 4, meaning a decrease of nearly 71.3%. Furthermore, snoring was reduced by 74.4% and there was a compliance rate of 89.3% compared to a reported 46 to 83% of patients being noncompliant to the traditional CPAP therapy.

Despite the foregoing options, there are really very few effective treatments available for central and mixed apneas which often comprise a significant portion of apneas, even in OSA patients.

Accordingly, what is needed is a device that can be universally applied to treat all three forms of sleep apnea, eliminates economical inefficiencies, and avoids negative side effects, while still adequately preventing apneic events and maximizing patient comfort. Manipulating atrial pressure of carbon dioxide in arterial blood ($PaCO_2$) should meet these criteria for the OSA patient. Accordingly, a device is needed which monitors and maintains $CO_2$ concentration levels during sleep, accordingly adjusting levels to prevent apneas, while also being easy to use, minimally invasive, and universally marketable.

SUMMARY

Sleep Apnea is a common sleeping disorder that affects over 25 million Americans (Xie et al 2013). Due to the complex nature of sleep apnea, and the human body, neither an effective nor comfortable treatment option for sleep apnea has been developed. Accordingly, the inventions described herein are a successful and novel alternative to current sleep apnea therapies, including CPAP therapy.

The sleep apnea therapy device disclosed herein incorporates the rebreathing of exhaled air to induce moderate hypercapnic conditions in systematic blood circulation. Advantageously, it eliminates apneic events in obstructive, central, and complex sleep apnea patients.

Generally, the sleep apnea therapy device is composed of a comfortable silicone rubber facemask that covers the mouth and nose, and flexible tubing that attaches to the anterior port of the mask. Moreover, this device counts apneas and automatically increases or decreases dead space (discussed in greater detail below) to minimize apneas, then sends reports to the clinician.

Accordingly, various embodiments of a device for reducing apnea are provided. A device for reducing sleep apnea is also disclosed which automatically increases inspired carbon dioxide by changing a volume of rebreathed exhaled air. In various embodiments, the disclosed device creates different $CO_2$ concentrations inside the device's reservoir for rebreathing. In one or more examples, the $CO_2$ concentration is measured at different volume intervals to determine the effect of dead space volumes on $CO_2$ concentrations.

More specifically, the device disclosed and shown in the Figures may include an inlet configured to accept exhaled air from a user of the device. The exhaled air comprises exhaled CO2. A sensor is provided and configured to detect an apneic event. A gas reservoir is also provided and configured to adjust dead space volume. The device includes at least one exit hole for expelling the exhaled air from the user of the device. A control unit is also provided which is configured to automatically adjust the dead space volume between the inlet and the at least one exit hole in response to the apneic event detected by the sensor. The control unit may also analyze data, record data, upload data, and/or transmit data obtained.

Disclosed herein is a sleep apnea therapy device that does not suffer from the problems of existing apnea therapies, and in particular CPAP machines. The device automatically adjusts the fraction of inspired carbon dioxide available to the use of the device to prevent sleep apnea. The disclosed device requires no blower and no increased pressure; therefore for these and other reasons it should be more widely accepted by patients.

A method for reducing apnea is further disclosed. The method includes providing a sleep apnea therapy device as described, identifying an apneic event with the sleep apnea therapy device, and adjusting the dead space volume of such device so as to reduce apnea in a patient.

These and other features and advantages of devices, systems, and methods according to this invention are described in, or are apparent from, the following detailed descriptions of various examples of embodiments.

BRIEF DESCRIPTION OF DRAWINGS

Various examples of embodiments of the systems, devices, and methods according to this invention will be described in detail, with reference to the following figures, wherein.

Figure 1:
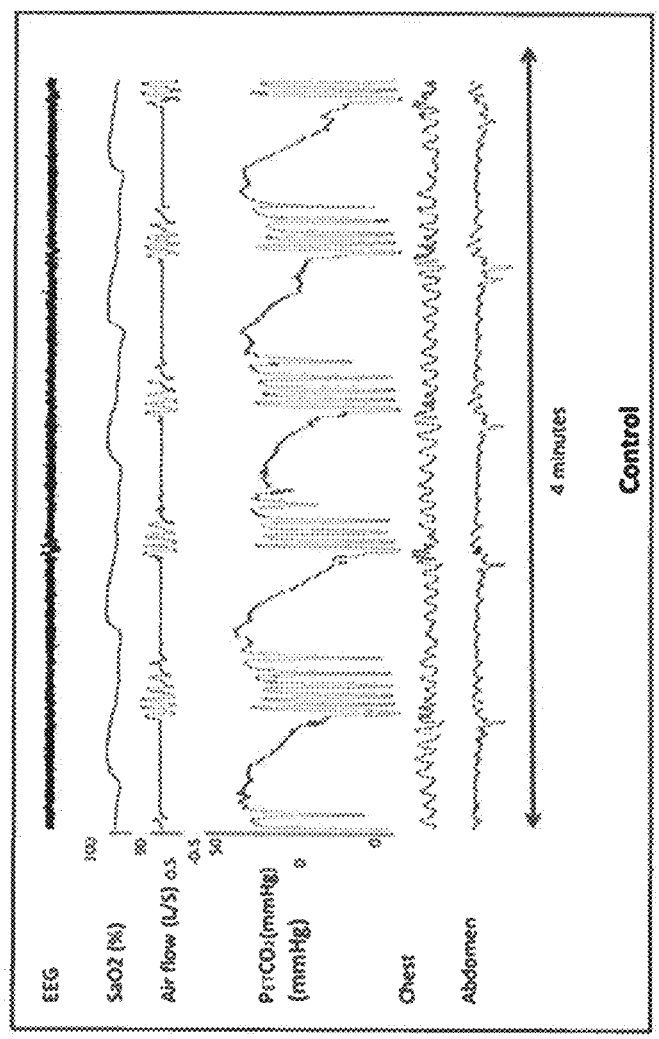
FIG. 1 is a chart illustrating observed experimental data under "control" conditions with repeated obstructive apneas.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

We have shown increases in end tidal carbon dioxide concentration ($P_{ET}CO_2$) of as little as 1 to 2 mmHg (achieved via rebreathing) to be highly effective in removing and preventing central apneas and periodic breathing induced by either high altitude hypoxia in health (Berssenbrugge 1983) or via CHF (Khayat 2003). Research at the University of Wisconsin, Madison (Xie et al 2013) concluded that increasing respiratory motor output using moderate hypercapnia conditions eliminated obstructive sleep apneic events in patients with moderate to highly collapsible airways and a wide range of $CO_2$ chemosensitivity. This was achieved through exposing the apnea patient to inhaled gas from a $CO_2$ reservoir; a process that increased $P_{ET}CO_2$ during normal breathing by 4.2±1 mmHg (range +2 to 5 mmHg). The main focus of Xie et al's research was on the Apnea-Hypopnea Index (AHI), a measure of the number of apneic episodes per hour. In 21 patients with moderate-to-severe obstructive and central apneas, all but 4 of those who received inhaled gas from a $CO_2$ reservoir showed a reduction in the AHI in excess of 30% below control. 17 of the 21 patients displayed extremely successful results, with a reduction of AHI by 94±3% of control with no significant impact on sleep state stability. Even OSA patients with extremely collapsible airways responded positively to the $CO_2$ treatment. Most of these results were obtained during periods of 4 to 6 h of $CO_2$ therapy during the night—but the findings were consistent with those obtained in a smaller number of patients studied throughout the night. Xie et al (2013) also utilized a system which sensed the transient overventilation phase which often precedes apnea and then switched the patient into a $CO_2$ reservoir system. This added small amounts of $CO_2$ thereby preventing transient hypocapnia and resulted in no change in the normal (normocapnic) $P_{ET}CO_2$.

This selective inhalation of gas from a $CO_2$ reservoir, i.e., an "isocapnic" system, reduced obstructive sleep apneas by 30% to 70% in 60% of the OSA patients. The results of these isocapnic treatments, and especially the modestly hypercapnic treatments in the OSA patients to date, suggest that a carefully regulated increase of 1 to 3 mmHg $P_{ET}CO_2$ would be effective and safe over long durations of time each night and over many nights in most patients with multiple obstructive, central and/or mixed apneas.

The rationale for using $CO_2$ manipulation as a treatment of OSA is based on two premises: a) preventing transient reductions in $PaCO_2$ will prevent the patient from reaching their apneic threshold; and b) raising $PaCO_2$ even a minimal amount provides a strong recruitment of upper airway dilator muscles (Dempsey 2010; Dempsey 2014), thereby preventing airway obstruction. In addition, a study conducted at John Rankin James Skatrud Sleep lab in Madison, Wis.'s Veteran's Administration hospital showed that continuous dead space rebreathing (an increase in anywhere from 2 to 5 mmHg of $CO_2$) led to the stabilization of the central respiratory output and prevented airway obstruction in a significant percentage of patients with mild to severe obstructive sleep apnea. This increase in $CO_2$ effectively stopped apneas from occurring during sleep.

Referring to the Figures, experimental data are shown illustrating different dead space rebreathing conditions. External dead space is defined as the volume of space contained within the user's mask, connecting tube, and reservoir ending at the outlet hole of the reservoir (said components are discussed in greater detail herein below). FIG. 1 illustrates experimental data under "control" conditions with repeated obstructive apneas. That is, under "control" conditions, periodic breathing with recurrent stagnation and no airflow (obstructive apneas), as well as frequent and dramatic dips in oxygen saturation occur. During the experiment, airway obstruction was confirmed through the paradoxical movements of the chest versus abdomen. When the chest expanded, the abdomen contracted, and as a result, no airflow between the upper airway and the lungs was seen and obstructive apneas occurred.

Figure 2:
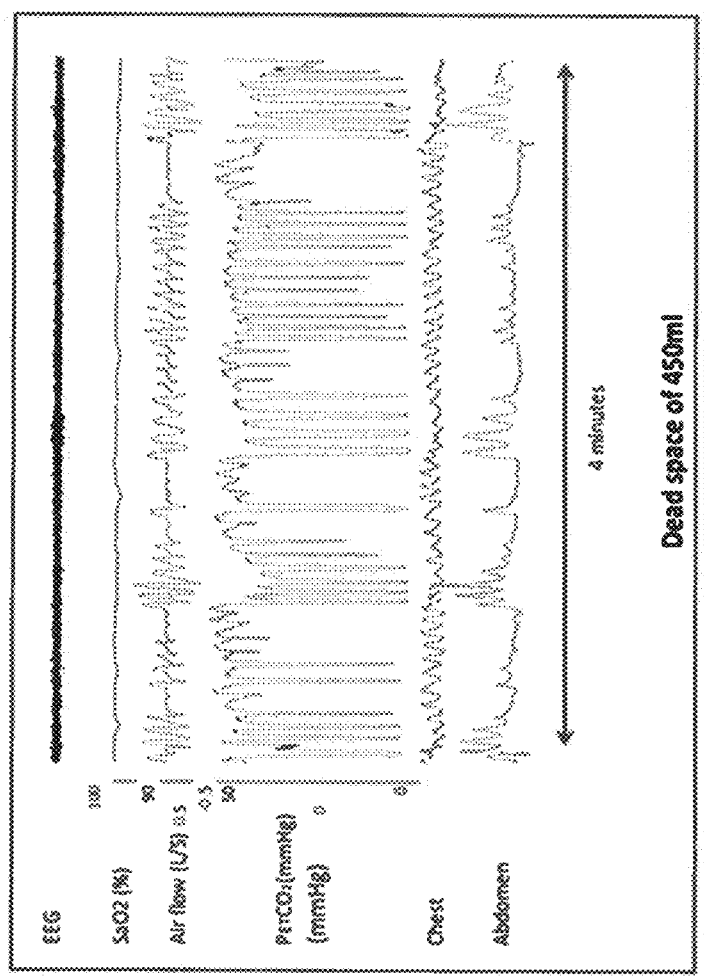
FIG. 2 is a chart illustrating experimental data under "low" dead space conditions (450 ml).

FIG. 2 illustrates experimental data under "low" dead space conditions (450 ml). In "low" dead space conditions, apneas and hypopneas are reduced below the control (FIG. 1), but many of the shorter duration events still exist. FIG. 2 shows under "low" dead space conditions, that respiration still demonstrated paradoxical chest versus abdomen movements, few apneic episodes, and several short hypopneas (decreases in $O_2$ saturation levels). It is also important to note that under "low" dead space conditions the post-hypopnea airflow increased significantly due to extra chemical stimulation.

Figure 3:
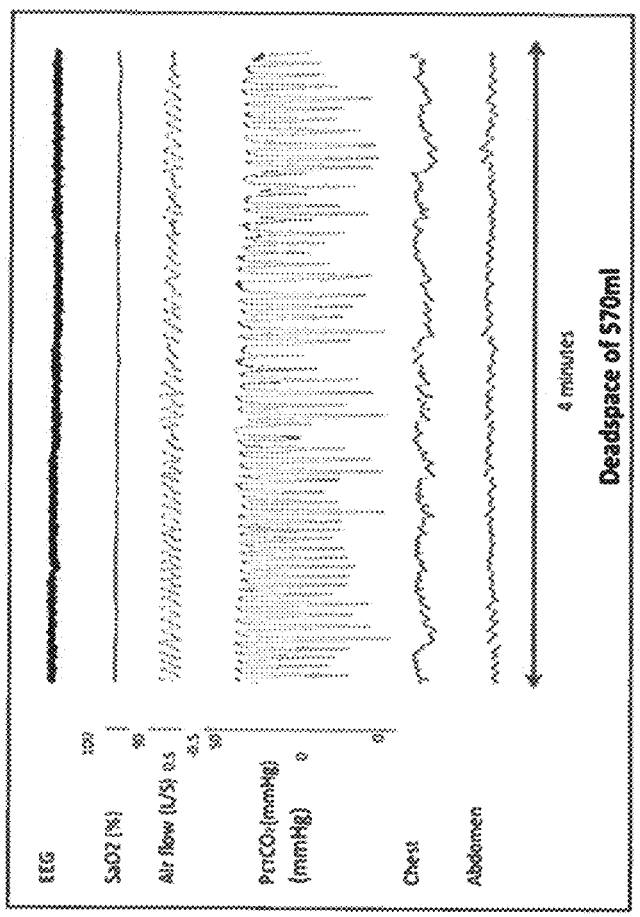
FIG. 3 is a chart illustrating observed experimental data under "high" dead space concentrations (570 ml).

FIG. 3 illustrates observed experimental data under "high" dead space concentrations (570 ml). In "high" dead space conditions, no apneas (i.e. time of zero flow) are present and only a few hypopneas remain. FIG. 3 illustrates that under "high" dead space conditions no apneas were observed. Additionally, no fluctuations in $O_2$ saturation were observed, indicating stable, steady breathing patterns. Airflow also remained relatively unchanged (compared to the previous two conditions)—as a result of the lack of hypopneas and related chemical-mechanical stimulations.

Figure 4:
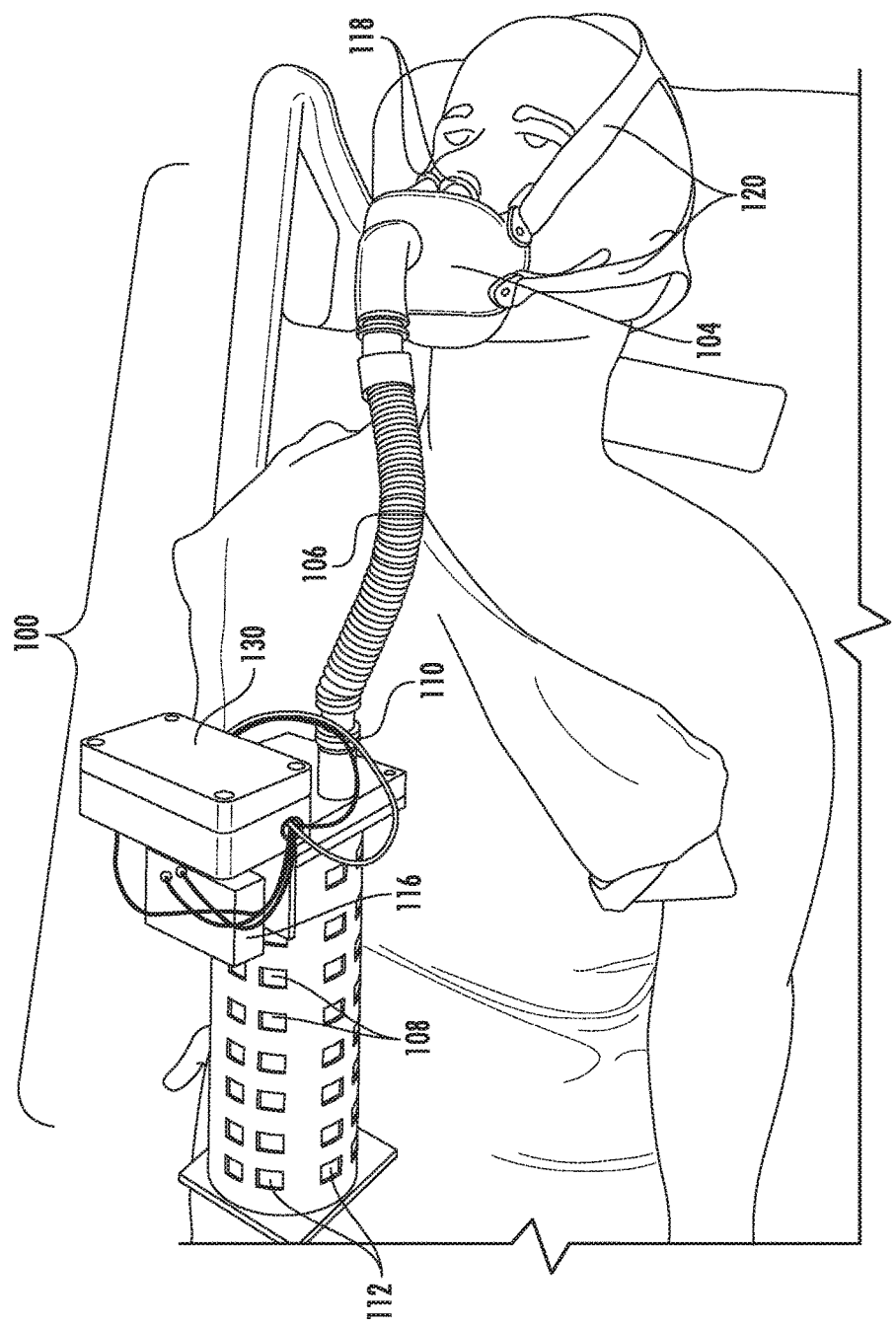
FIG. 4 is a perspective use of a sleep apnea therapy device according to one or more examples of embodiments in use by a user.

Accordingly, a device for reducing apnea is provided. More specifically, a sleep apnea therapy device 100 is provided which is configured to automatically adjust dead space 102 volume. Generally, as shown in FIG. 4, the sleep apnea therapy device 100 includes a mask 104 to cover the wearer's mouth and nose. The mask 104 is connected via a flexible tube 106 to a variable sized reservoir 108 that has an inlet 110, connected to the tube 106, and an outlet 112 which is open for fresh air ventilation. The inlet 110 is configured to accept exhaled air from a user of the device 100. The exhaled air comprises exhaled $CO_2$. The distance between the inlet 110 and outlet 112 is adjustable. In order to accomplish the adjustable distance forming the dead space 102 volume, the sleep apnea therapy device 100 includes a variably sized reservoir 108. Namely, the reservoir 108 may be a gas reservoir which may be configured to adjust dead space 102 volume as more fully described herein below. The device, and in particular the reservoir 108, may include at least one outlet or exit hole 112 for expelling the exhaled air from the user of the device.

A sensor 114, or more than one sensor, may be provided and configured to detect an apneic event. The apneic event may be an apnea or a hypopnea, or the apneic event may be the absence of an apnea (e.g., the temporary cessation of breathing) or a hypopnea (e.g., abnormally slow or shallow breathing). For example, as discussed in more detail below, one or more sensors 114 provided in the airstream that measure the flow rate of each breath of the wearer and may sense the slowing or cessation of breathing or a reduction in airflow. A control unit or controller 116 is also provided which is configured to automatically adjust the dead space 102 volume between the inlet 110 and the at least one exit hole 112 in response to the apneic event detected by the sensor 114. That is, the controller 116 interprets sensed data received from the sensor 114 as an apneic event and instructs the motor or pump or valve 130 to activate and adjust dead space 102 volume.

Figure 9:
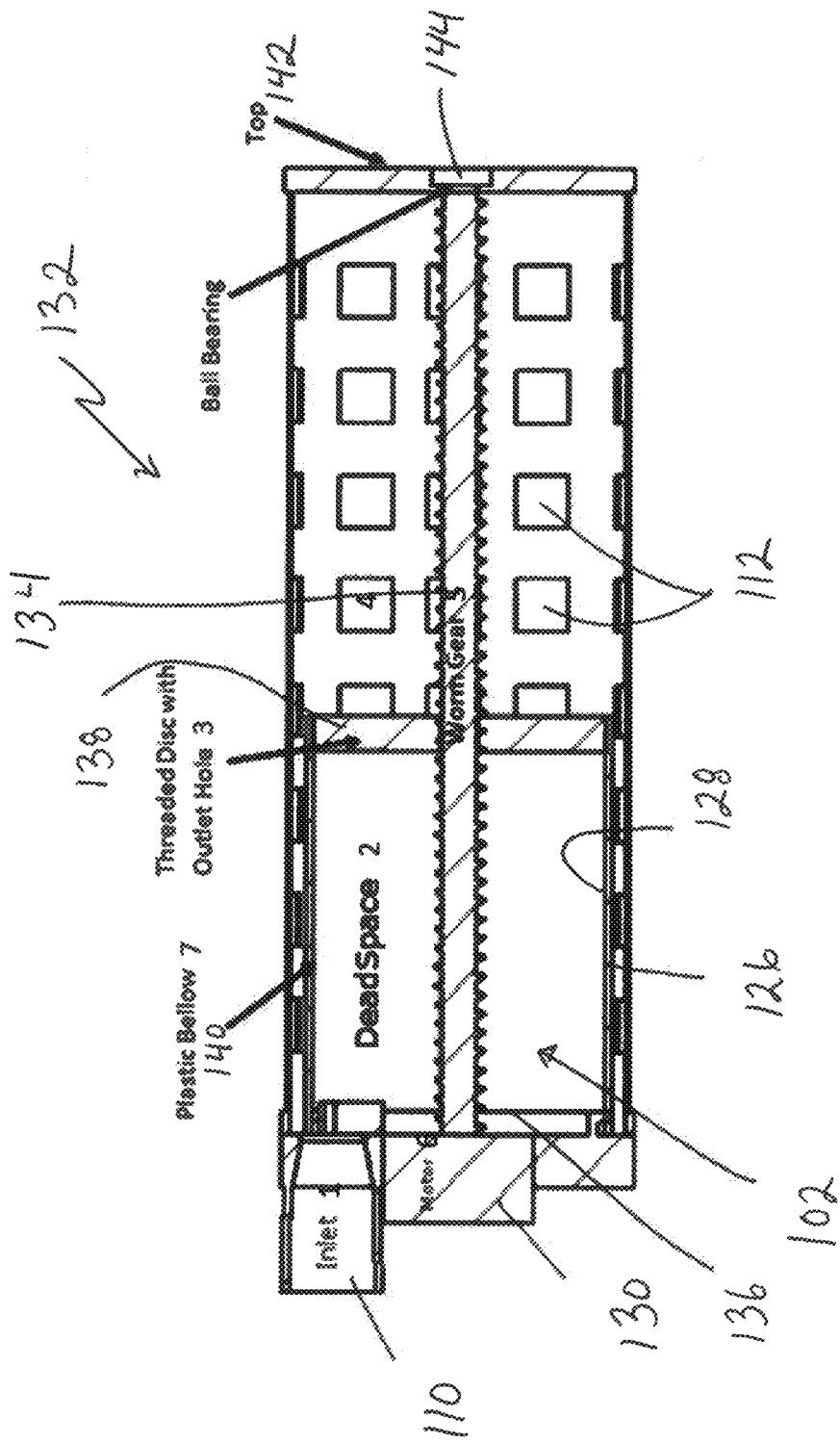
FIG. 9 is a cross-sectional view of a gas reservoir according to one or more alternative examples of embodiments, showing an accordion-like collapsed bellows that can be expanded and contracted.
Figure 10:
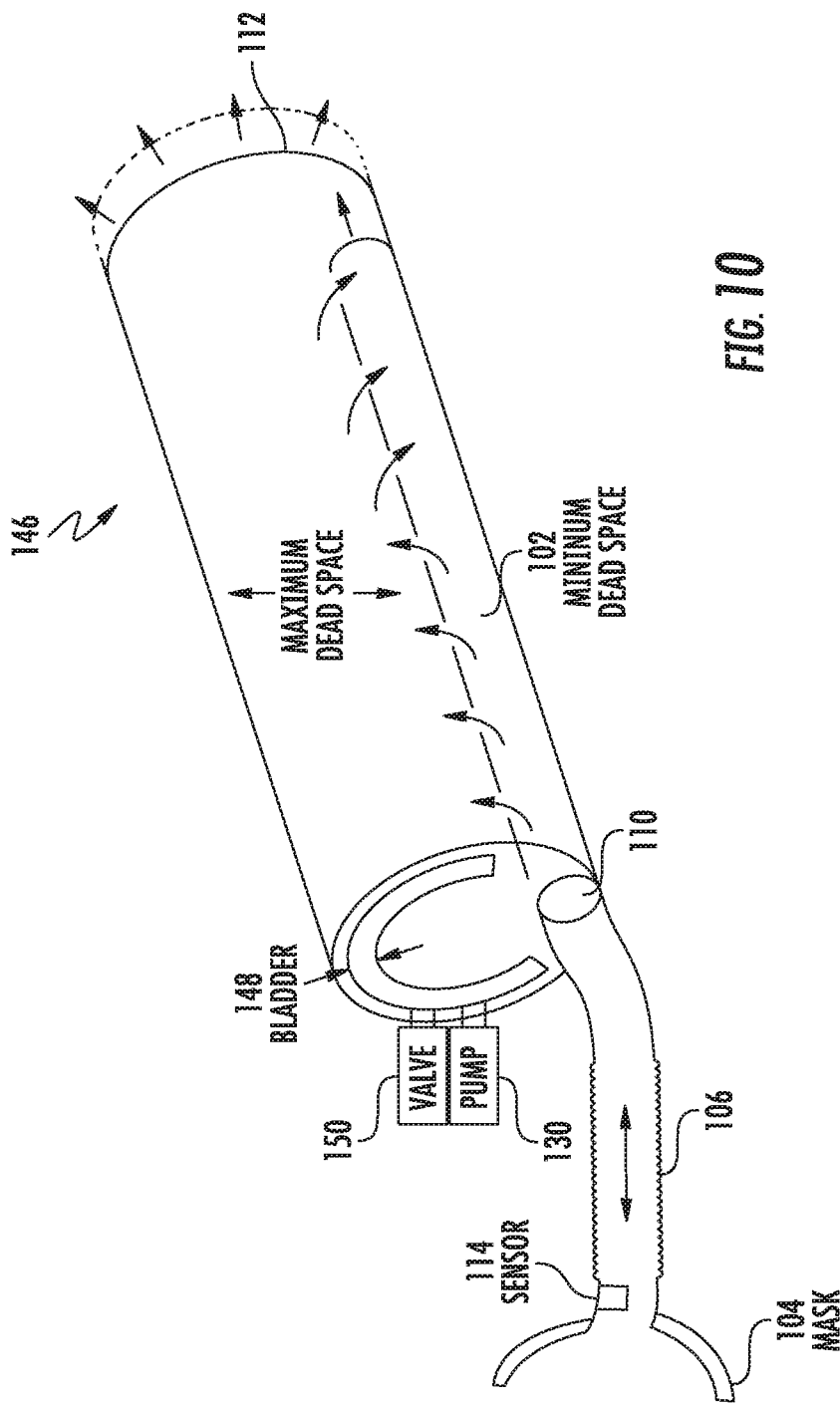
FIG. 10 is a partial perspective view of a sleep apnea device according to one or more examples of embodiments, showing a gas reservoir having a pump, valve and bladder.

As indicated, the sleep apnea therapy device 100 disclosed herein and shown in the Figures includes an inlet 110 configured to accept exhaled air (e.g., exhaled $CO_2$) from a user of the device. To this end, the inlet 110 is composed of a facemask 104 which covers the mouth, the nose, or both the mouth and nose of a user of the device. Example facemasks 104 are shown in FIGS. 4, 9, and 10. As can be seen in the Figures, the facemask 104 is composed of a body contoured to cover the mouth and/or nose of the user. The facemask 104 may be disposable/replaceable. The facemask 104 may be rigid or flexible, or semi-flexible. For example, the facemask 104 may be made out of a semi-flexible plastic material. The facemask 104 may also optionally include a cushioned surface around its outer edge, which may provide for additional user comfort. In one or more alternative examples of embodiments, the sleep apnea therapy device 100 utilizes existing nasal masks 118 (or nasal tubes) used in some forms of CPAP therapy (see FIG. 4). Generally, the facemask 104 allows for breathing to occur through either the mouth or nose, subject to an increased volume of rebreatheable dead space 102, and an increased level of comfort.

The device 100 and in particular the mask 104 utilizes stability straps 120, which are intended to hold the device (specifically the facemask) in the same location at the patient's/user's/wearer's nose and/or mouth for the entire length of time worn by the user. For example, the facemask 104, in one or more examples of embodiments, includes one or more head straps 120 which attach to the facemask 104 and are configured to wrap around a portion of the user's head. The head straps 120 may be fixed in length, or may be variable in length, and in one or more examples of embodiments, the head straps 120 may be elastic or may have a degree of elasticity.

Advantageously, the mask 104 increases dead space 102 while minimizing the effort needed to breathe. Second, as the sleep apnea therapy device 100 does not require increased air pressure, it allows for more comfort in the mask 104 during overnight wear (e.g., eliminating the increased pressure used in many CPAP therapies).

Figure 5:
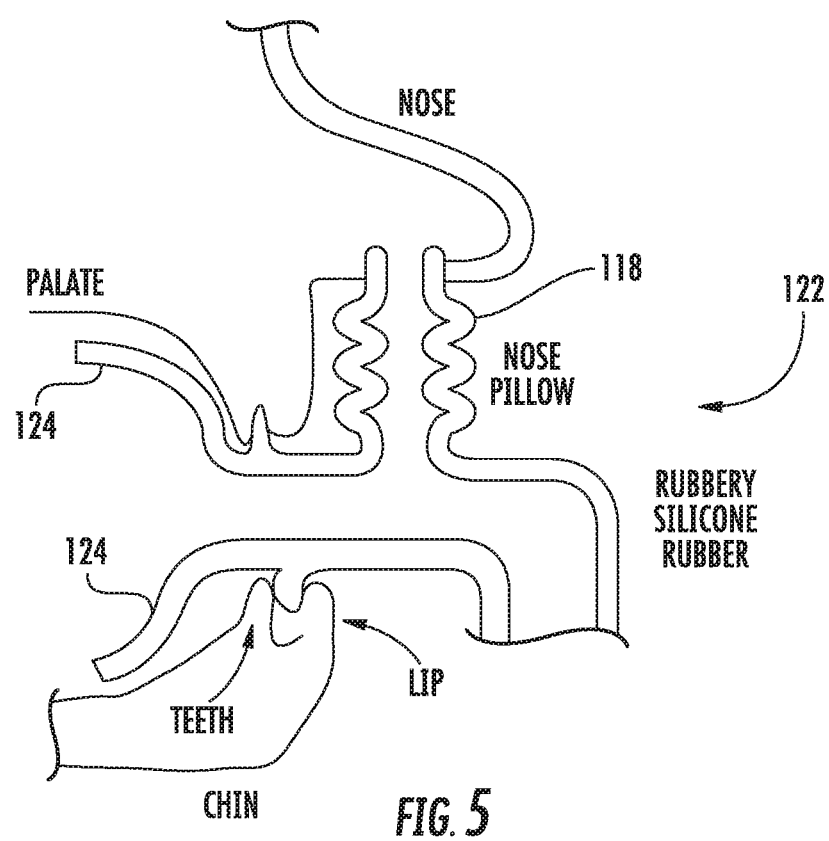
FIG. 5 is a cross-sectional elevation view of one or more alternative examples of a mouthpiece for use with the sleep apnea therapy device, showing the mouthpiece in use by a user.

In one or more alternative examples of embodiments, the inlet 110 of the sleep apnea therapy device 100 is composed of a mouthpiece 122 configured to permit a user of the device to use the device without head straps (see FIG. 5). To this end, the mouthpiece 122 comprises a flange 124 configured to expand within a mouth of a user of the device and nose pillows 118. FIG. 5 illustrates a rubbery silicone rubber mouthpiece 122 that expands within the mouth of the user, plus nose pillows 118. Because it is supported or retained by the user's mouth and nose, the mouthpiece 122 does not require head straps; that is, the mouthpiece is arranged and supported on the user without head straps.

Figure 6:
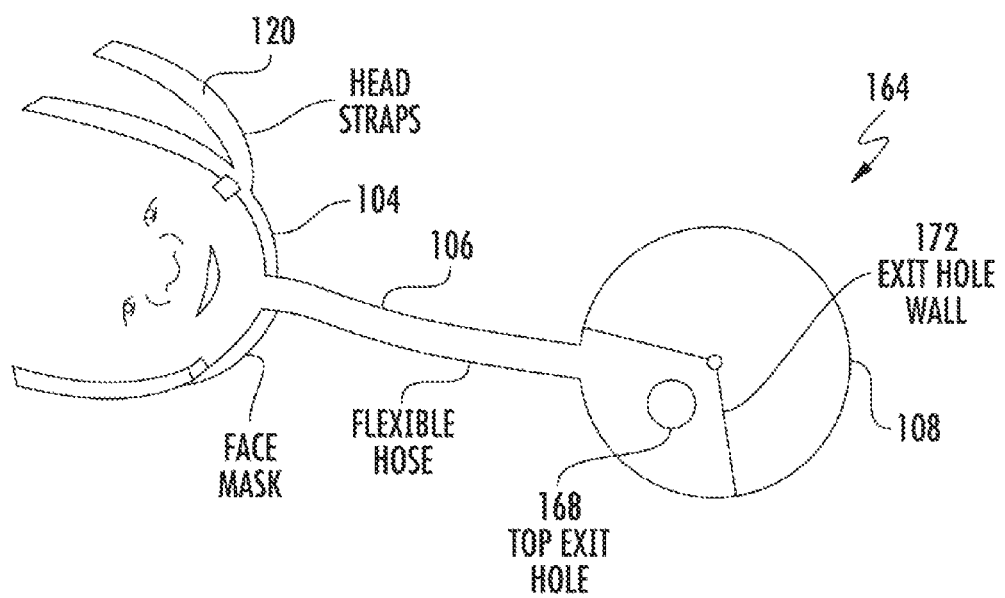
FIG. 6 is a top elevation view of a sleep apnea therapy device according to one or more alternative examples of embodiments in use by a user, showing a gas reservoir which is a cylindrical reservoir, and in which a top exit hole and the exit hole wall automatically move counterclockwise to lengthen dead space.
Figure 7:
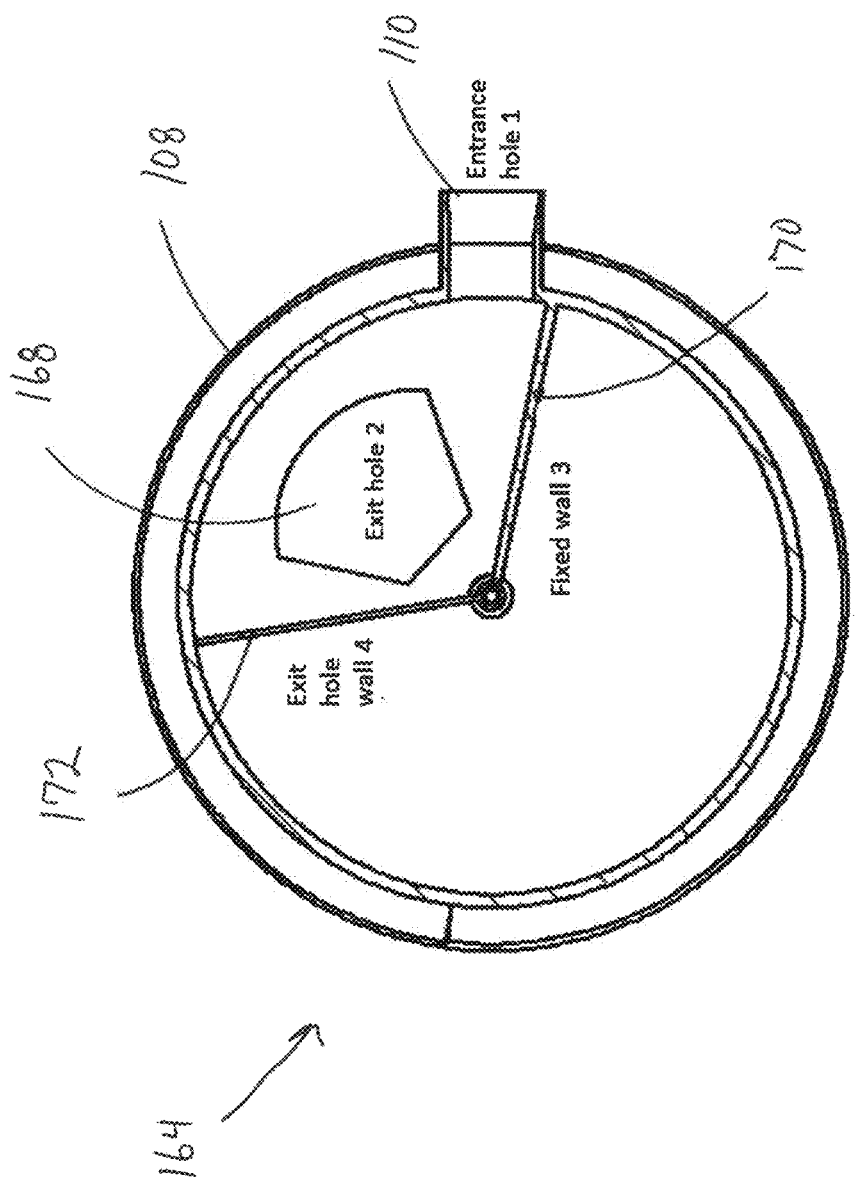
FIG. 7 is a top elevation view of the gas reservoir according to various examples of embodiments, which is a cylindrical reservoir shown in FIG. 6.
Figure 8:
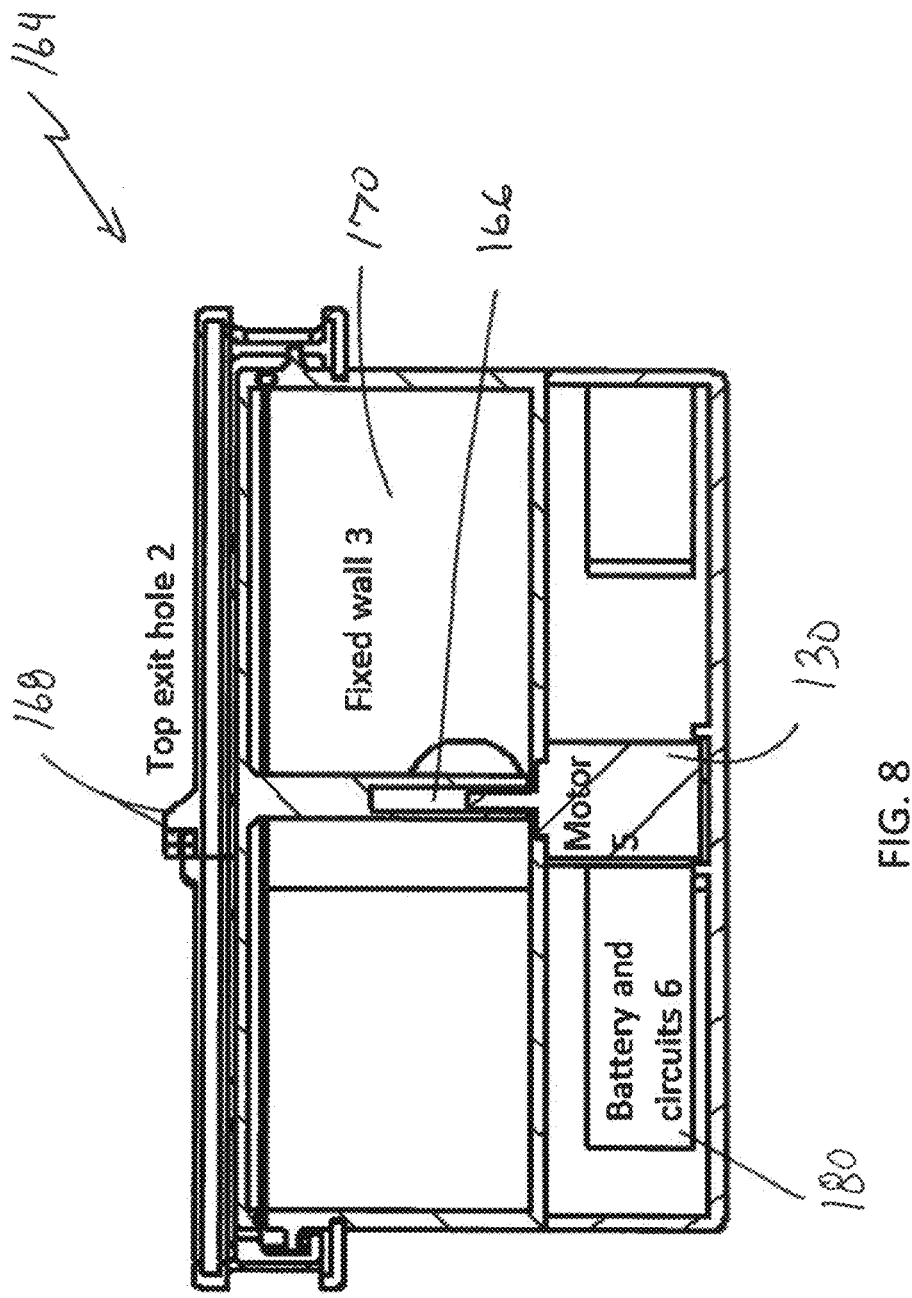
FIG. 8 is a side cross-sectional view of the gas reservoir shown in FIG. 7 according to various examples of embodiments, illustrating a compact design having a motor at the bottom of the reservoir, driving a vertical shaft that rotates a top disk with an exit hole covered with mesh.

Referring to FIGS. 6 to 8, in one or more examples of embodiments, the facemask 104 is joined to the gas reservoir 108 by a flexible hose or tube 106, which couples to the entrance hole or aperture or inlet 110 on the reservoir 108 (see FIG. 7). More specifically, the mask 104 is connected via a flexible tube 106 to the variable sized reservoir inlet 110. The flexible hose or tube 106 is hollow and permits the transfer of gas (e.g., is a conduit), in particular $CO_2$ between the user and inlet 110 and reservoir 108. The tube 106 or hose may be disposable/replaceable. The tube 106 may be integrally formed with the facemask 104 and/or reservoir 108 or may be separately formed and attached. Preferably the flexible hose or tube 106 is tightly secured and/or sealed to prevent the entry exit of gas from said connections.

Additionally, in one or more examples of embodiments a filter (not shown) may be provided between the facemask 104 and the variable reservoir 108. The filter may be provided to filter exhaled breath from the wearer before entering the tubing 106 or reservoir 108 and dead space 102 as well as inhaled breath by the user.

As indicated and shown in FIGS. 4, 6 to 12, the sleep apnea therapy device 100 may include one or more outlets or exit holes 112 for expelling the exhaled air from the user of the device. Preferably, the exit holes 112 are distributed on the gas reservoir 108 in locations suitable for the expelling of exhaled air. Likewise, exit holes 112, which are apertures into the gas reservoir 108, may serve as conduits for external or "fresh" air into the sleep apnea therapy device 100 such that the user may receive a supply of fresh air.

As indicated herein, a gas reservoir 108 which is a variable volume reservoir is provided with the sleep apnea therapy device 100. Examples of gas reservoirs 108 are shown in FIGS. 4, 6 to 12. As will be discussed in greater detail below, preferably, the gas reservoir 108 is configured to adjust dead space 102 volume; that is, the gas reservoir is a variable volume dead space reservoir. Examples of variable volume reservoirs 108 include, but are not limited to: a fixed volume plus bladder (or more than one bladder) reservoir (FIG. 10), a reservoir having a rotatable chamber or more than one rotatable chamber (FIGS. 6, 7 and 8), an expandable bellows reservoir (FIG. 9), a reservoir having one or more tubes capable of telescoping (FIG. 11), and the like, as well as combinations of the foregoing. In this regard, the gas reservoir 108 is generally composed of a housing 126 forming an interior cavity 128. The interior cavity 128 has a volume. It is contemplated that the gas reservoir 108, and in particular, the housing 126 forming an interior volume or cavity 128, may be a fixed volume. The interior cavity 128 may include one or more mechanical systems that adjust the interior volume which makes up the dead space 102. That is, in one or more examples of embodiments the device includes one or more mechanisms for automatic variable dead space 102 volume adjustment, which allows for incremental adjustments to vary the dead space volume.

Accordingly, the sleep apnea therapy device 100 may include a motor 130 or pump or valve, which may be engaged with a corresponding mechanical system to drive the adjustment of the interior volume. Referring to FIGS. 4, 8 to 12 a motor 130 or pump may be provided and configured to adjust the dead space 102 volume. While the motor 130 or pump is provided to adjust dead space 102 volume, preferably, the sleep apnea therapy device 100 does not comprise a blower, nor does it provide for positive airway pressure. The motor 130 (FIG. 4, 8, 9, 11, 12) or pump 130 (FIG. 10) or valve (FIG. 10, 12) may be any suitable commercially available device which accomplishes the purposes of driving the change of volume within the reservoir 108, is controllable, and is preferably sized to fit on a portable system. In the embodiments described in further detail herein below, the motor 130 or valve or pump is connected to a controller 116 (FIG. 13). In response to a command or instructions received from the controller 116, the pump or motor 130 or valve activates to translate motion or adjustment of a component of the gas reservoir 108. Accordingly, a device for reducing sleep apnea is provided that may automatically increase inspired carbon dioxide by mechanically changing a volume of rebreathed exhaled air.

In one example shown in FIG. 9, the reservoir 132 consists of a worm-gear driven bellow tube which allows the contraction and expansion of a constant diameter cylinder to a desired volume. In this embodiment, a motor 130 is mounted to the housing 126 of the reservoir 132. The worm gear 134 is attached to the motor 130 via a hole or aperture on the wall 136 of the reservoir housing 126. A threaded disc 138 that acts as the outlet 112 for the dead space 102 is attached (e.g., screwed or threaded) onto the threaded shaft of the worm gear 134. A bellow 140, which may be a plastic bellow or other suitable material, is stretched over the threaded disc 138 and secured to a lip at the wall 136 of the reservoir that includes or encompasses the inlet 110 hole. A top 142 of the housing 126 of the reservoir 132 is secured on the opposite side of the reservoir, closing the reservoir 136 and receiving and centering the worm gear using a ball bearing 144. A processor or microprocessor such as controller 116 may be mounted in an electronics container, which is mounted to the housing 126 to process sensor 114 data and control the motor 130.

In another example of a reservoir 146, shown in FIG. 10, the interior cavity 128 has an inflatable/deflatable bladder 148. The bladder 148 may be inflated by gas (or fluid in certain examples of embodiments) so as to change the interior cavity volume of the gas reservoir 146 shown in FIG. 10. The bladder 148 may therefore be coupled to a pump, a blower, a fan, or other device 130 for effecting the movement of gas/fluid into and out of the bladder. For example, in FIG. 10 the bladder is in fluid communication with a pump 130 (for inflation) and valve 150 (for deflation). The bladder 148 therefore also may include an aperture or inlet 110 and an outlet 112 (which may be the same or different apertures). The bladder 148 may also be composed of one or more compartments, which may be individually or separately inflated/deflated.

Figure 11:
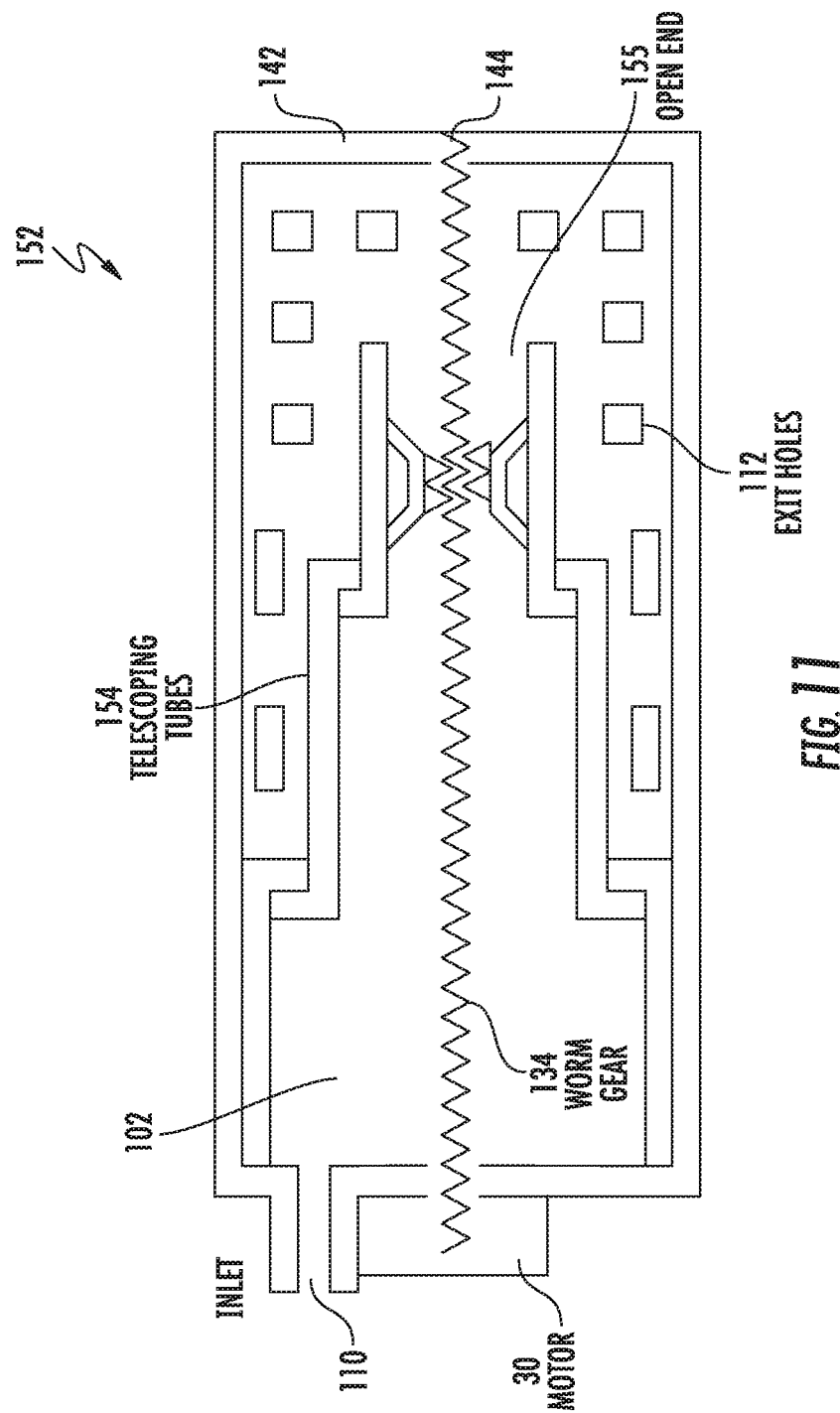
FIG. 11 is a cross-sectional view of one or more alternative examples of embodiments of a gas reservoir, showing a motor, which may drive a worm gear that expands and contracts a telescoping tube.

Similarly, in another alternative example of a reservoir 152, shown in FIG. 11, in place of an expandable bellows as described above, the interior cavity 128 may have a telescoping tube or telescoping components 154. The telescoping components 154 may be expanded or contracted (moved relative to one another) to adjust the interior cavity volume and in particular the dead space 102 volume. To this end they may be coupled to a motor 130 for driving the telescoping movement.

Figure 12:
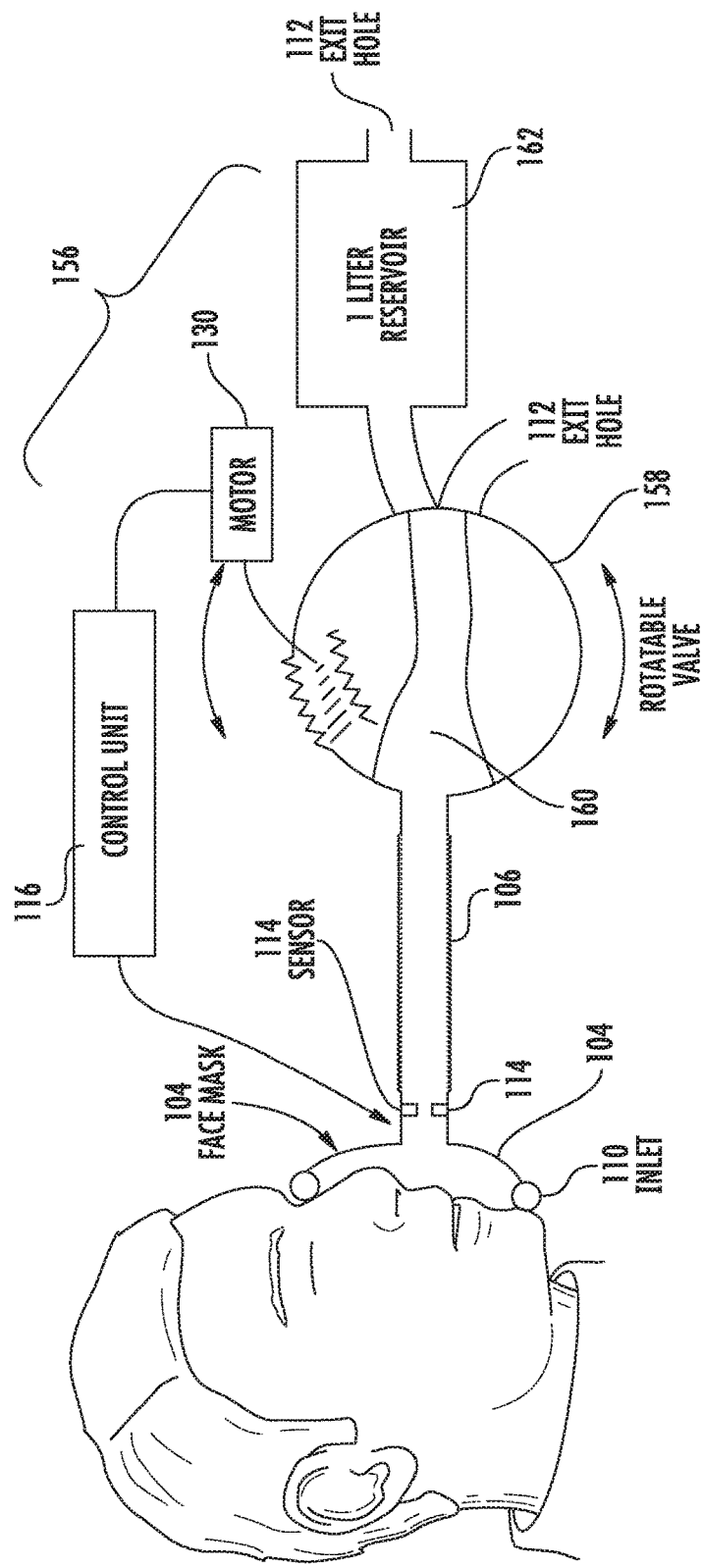
FIG. 12 is a partial elevation view showing sleep apnea therapy device according to various examples of embodiments having a reservoir formed of a mixing valve which blends inhaled gas from both a gas reservoir and from one or more exit holes.
Figure 13:
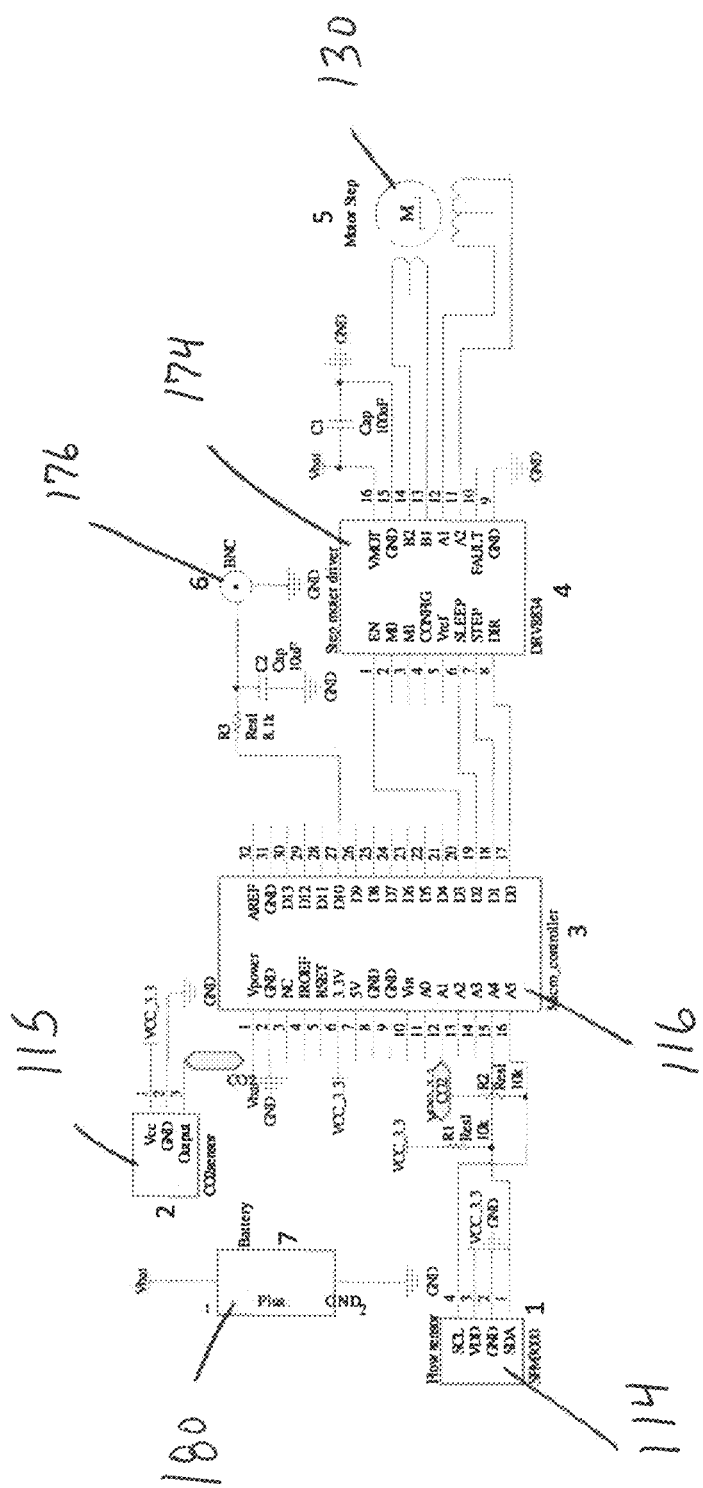
FIG. 13 is an electrical circuit diagram of a sleep apnea therapy device according to one or more examples of embodiments.

In another example of a reservoir 156, shown in FIG. 12, the interior cavity 128 has a rotatable valve 158 which blends inhaled gas from both a gas reservoir and one or more exit holes. As can be seen in FIG. 12, a motor 130 is joined to the housing 126 of the reservoir 156 and drives rotation of a rotatable valve 158. The valve 158 may be or include a passage or opening or channel 160 for transmission of air/$CO_2$ which may be aligned with a fixed reservoir 162. The valve 158 may be rotated to completely or partially align with the fixed reservoir 162 and an exit hole 112 on the reservoir 156, thereby controlling the respective flows. In this embodiment, the sleep apnea therapy device 100 is therefore provided with a valve that blends inhaled gas from both a gas reservoir 162 and from one or more exit holes 112. FIG. 12 illustrates that a mixing valve 6 blends inhaled gas from both a gas reservoir 162 and gas drawn into the device from one or more exit holes 112. As a non-limiting example, the valve 158 may function in a similar manner as the mixing valve in a bathroom shower that blends hot and cold water to yield warm water. As one illustration in reference to FIG. 12, inlet 110 through facemask 104 draws inhaled gas through sensor 114, which may be an airflow sensor. Upon receipt of sensed data from the sensor 114, controller or control unit 116 drives stepping motor 130, which rotates a worm gear. The rotation of the worm gear rotates mixing valve 158 to align the channel 160 within the valve with the respective air/$CO_2$ source.

Referring again to FIGS. 7 and 8, one or more further alternative examples of embodiments of a reservoir 164 are shown. FIG. 5 illustrates a cylindrical reservoir 164 that is compact, having a motor 130 at the bottom of the reservoir, driving a vertical shaft 166 that rotates a top exit hole 168 covered with mesh. As motor 130 rotates the top exit hole 168 counterclockwise away from fixed wall 170, exit hole wall 172 moves with top exit hole 168 to increase dead space 102 between entrance hole 110 and top exit hole 168.

In one or more alternative examples of embodiments, a single mixing valve could be replaced by two or more valves (not shown), which may be used to permit rebreathing dead space gas at the optimal time prior to breathing fresh air. For example, Giannoni et al (2010) has shown that squirting 100% $CO_2$ at the optimal time during the inhalation phase reduces voluntary induced apneas in normal subjects while maintaining the average $P_{ET}CO_2$ near normocapnic levels. A similar approach, whereby the automated system delivers $CO_2$ at the optimal time to the patient/user may be used. Such an approach may minimize the arousal that may result from continuously elevated $CO_2$.

As indicated, a sensor 114 may be provided on or within the sleep apnea therapy device 100 which is configured to detect an apneic event. One sensor 114 or a plurality of sensors may be provided and used. More specifically, the sleep apnea therapy device 100 includes one or more sensors 114 provided in the airstream that measure the flow rate of each breath of the wearer in order to provide feedback to guide the amount of dead space 102 volume available for rebreathing. As shown in FIGS. 9, 10 and 12, one or more sensors 114 may be provided on or near the facemask 104 or exit opening of the facemask, or alternatively in the flexible tube 106. In one or more examples of embodiments, the sensor(s) 114 is a flow sensor, a velocity sensor, a $CO_2$ sensor, or a sound sensor, and the like, as well as combinations of the foregoing, which sensor(s) may be positioned in the sleep apnea therapy device in a location suitable for detection of the relevant parameter. The sensor may also be a pulse oximeter, a thermal sensor, an optical sensor, or the like, or combinations of the foregoing, as well as combinations of any of the sensors described herein. Accordingly, apneas may be detected, for example by pulse oximetry, or a thermal flow sensor (such as hot wire anemometer), or an optical sensor (such as that detects movement of a drag sensor), or a flow sensor (such as a pneumotachometer). The foregoing sensors detect relevant data detectable by such a device by now known or future developed means and deliver sensed data in one or more packets to the controller. While specific examples of devices and locations are provided, variations thereon may be acceptable without departing from the overall scope of the present invention.

The sleep apnea therapy device 100 disclosed in one or more preferred embodiments uses a feedback process and system using one or more sensors 114, as indicated above, which are in communication with a controller 116 inside, on, or proximate the device. The sensors 114 may be directly connected (wired) or may be wirelessly connected to the controller 116. The sensors 114 and controller may be used, for example, to: (1) accelerate the sleep apnea healing process by stimulation of chemoreceptors which are sensitive to $CO_2$ levels at or near the apneic threshold—through control of the volume of rebreatheable $CO_2$; (2) prevent the apneic events by providing adaptable, controlled exposure of exhaled $CO_2$ for different patient requirements; (3) monitor the curing process for symptoms of both obstructive and central sleep apnea; (4) operate as an independent device with no required $CO_2$ tank; and/or (5) relay the information wirelessly to a central location for storage and interpretation by a physician. While specific examples are provided above, additional benefits and solutions may also be developed or apparent from the present invention.

As indicated, a control unit or controller 116 is provided which is configured to automatically adjust the dead space 102 volume between the inlet 110 and the at least one exit hole 112 in response to an apneic event detected by a sensor 114. To this end, the control system or controller 116 of the sleep apnea device is configured to analyze data, record data, upload data, and/or transmit data, as well as combinations of the foregoing. In one or more particular examples of embodiments, the controller 116 is configured to analyze data as a function of time, upload data as a function of time, and/or transmit data as a function of time, as well as combinations of the foregoing. Generally, when the controller 116 receives and analyzes data identifying more than a threshold number of sensed apneas per hour, the controller 116 increases dead space 102 volume within the sleep apnea therapy device 100 reservoir 108; and when the controller 116 receives and analyzes data identifying fewer than a threshold number of sensed apneas per hour, the controller 116 decreases the dead space 102 volume within the sleep apnea therapy device 100 reservoir 108. Thus, the device adapts to different patients/users, to a change in physiology from beginning sleep to deeper sleep, etc.

The control unit 116 (FIG. 13) in one or more examples of embodiments includes a microcontroller. In one or more further examples of embodiments, a non-transitory computer readable storage medium is provided having stored thereon a computer program for controlling the adjustable dead space 102 volume of the reservoir 108. The computer program has and executes a set of instructions that instruct the device to perform or execute one or more of the following steps: (a) identify an apneic event; and (b) adjust the dead space 102 volume. In one or more examples of embodiments, the apneic event may be an apnea or a hypopnea, or the apneic event may be the absence of an apnea or a hypopnea. In addition to the foregoing, the control unit or controller 116 may receive and analyze data versus time. Likewise, the control unit 116 may have a means to communicate data, such as, but not limited to, a Bluetooth communication module, a Wi-Fi communication module, a USB port, and the like, and may therefore transmit data to a remote location (and may receive data from a remote location).

The control unit or controller 116 automatically adjusts the dead space 102 volume from a first dead space volume to a second dead space volume. In one or more further examples of embodiments, the control unit 116 automatically adjusts the dead space 102 volume from a second dead space volume to a first dead space volume. The second dead space volume in one example is larger than the first dead space volume. However, the first dead space volume may be larger than the second in another example of embodiments. According to the examples of embodiments described herein, the adjustment to the dead space 102 volume results in a change in the inspired $CO_2$.

As indicated, in one or more examples of embodiments the system and/or method may be implemented by a microcontroller, a computer system, or in combination with a computer system. The computer system may be or include a processor. The computers may be electronic devices for use with the methods and various components described herein and may be programmable computers which may be special purpose computers or general purpose computers that execute the system according to the relevant instructions. The computer system or portable electronic device can be an embedded system, a personal computer, notebook computer, server computer, mainframe, networked computer, workstation, handheld computer, as well as now known or future developed mobile devices, such as for example, a personal digital assistant, cell phone, smartphone, tablet computer, and the like. Other computer system configurations are also contemplated for use with the communication system including, but not limited to, multiprocessor systems, microprocessor-based or programmable electronics, network personal computers, minicomputers, smart watches, and the like. Preferably, the computing system chosen includes a processor suitable in size to efficiently operate one or more of the various systems or functions or attributes of the communication system described.

The system or portions thereof may also be linked to a distributed computing environment, where tasks are performed by remote processing devices that are linked through a communication network(s). To this end, the system may be configured or linked to multiple computers in a network including, but not limited to, a local area network, wide area network, wireless network, and the Internet. Therefore, information, content, and data may be transferred within the network or system by wireless means, by hardwire connection, or combinations thereof. Accordingly, the servers described herein communicate according to now known or future developed pathways including, but not limited to, wired, wireless, and fiber-optic channels.

Data, for example, sensor data or recommendations, may be sent or submitted via the Internet, wireless, and fiber-optic communication network(s), or created or stored on a particular device. In one or more examples of embodiments, data may be stored remotely or may be stored locally on the user's device or controller. In one example, data may be stored locally in files. Data may be stored and transmitted by and within the system in any suitable form. Any source code or other language suitable for accomplishing the desired functions described herein may be acceptable for use.

Furthermore, the computer or computers or portable electronic devices may be operatively or functionally connected to one or more mass storage devices, such as but not limited to, a database. The memory storage can be volatile or non-volatile, and can include removable storage media. Cloud-based storage may also be acceptable. The system may also include computer-readable media, which may include any computer-readable media or medium that may be used to carry or store desired program code that may be accessed by a computer. The invention can also be embodied as computer-readable code on a computer-readable medium. To this end, the computer-readable medium may be any data storage device that can store data which can be thereafter read by a computer system. Examples of computer-readable medium include read-only memory, random-access memory, CD-ROM, CD-R, CD-RW, magnetic tapes, flash drives, as well as other optical data storage devices. The computer-readable medium can also be distributed over a network-coupled computer system so that the computer-readable code is stored and executed in a distributed fashion.

As indicated, a display (not shown) may be provided for display of data. To this end, a screen may be provided as part of the system. The screen may be a tablet or mobile computing device. The screen may transmit or receive data over Wi-Fi or Bluetooth. The screen may be positioned where a user may observe the screen data.

Additionally, information may be stored in the system such that data can be used to provide feedback. In various embodiments, data may be stored in the screen, computing device, mobile device, or other suitable location.

After the sensors 114 detect the presence or absence of certain attributes in the user's breath (e.g., airflow or velocity), the data could be passed to the microcontroller 116 and/or a linked computing device. Sensors may perform periodic sampling or may provide data upon each sensed event to the microcontroller. The microcontroller 116 or computing device may receive information from the one or more sensors. The microcontroller 116 or computing device may analyze the data and apply certain recommendations or instructions.

Sensed and/or analyzed data or information stored in the microcontroller 116 or computing device may be sent to a screen/display (not shown) or a third party application (e.g., to a user's or a physician's data collection software application). In one example, from the screen or application, the user could decide whether to send the information to a physician or hospital, or the microcontroller or computing device may send such information or data directly to the physician or hospital. Communication by or between the microcontroller 116 or computing device and various receiving entities described could be made possible by use of Wi-Fi, Bluetooth, or other suitable transmission mechanism.

The system may include a display provided on a user feedback screen (not shown). After the data is sensed, the data (which may be stored data) or any analytical results may be displayed by the microcontroller on the screen, or alternatively or additionally on an application, such as a tablet, mobile device, or phone application. The display may show data results, as well as feedback for the user based on the data. Sending the result to a physician may be optional to the user either via email or personal electronic file.

Referring to FIG. 13, an electrical circuit diagram of one or more examples of a controller 116 is shown. As can be seen, a microcontroller 116 is coupled to various devices. While one microcontroller 116 is shown, in one or more examples of embodiments, more than one microcontroller may be used. As seen in FIG. 13, a sensor 114, such as a flow sensor or more than one flow sensor (e.g., two or more) which detect moving air and/or detect apnea, is in electrical communication with the microcontroller 116 such that it may communicate such detected data to the microcontroller 116. A $CO_2$ sensor 115 may also be provided to detect $CO_2$ concentration and be in electrical communication with the microcontroller 116 for measurement thereof. In one or more examples of embodiments, two or more $CO_2$ sensors may be provided. A driver 174 (or more than one driver) is also in electrical communication with the microcontroller 116 and is in electrical communication with a motor 130 to drive or power the motor 130. As described herein, the motor 130 drives the variable volume dead space adjustment mechanism (discussed above) and thereby changes the dead space 102 within the gas reservoir 108. A connector 176 is also provided in electrical communication with the microcontroller 116 and also in electrical communication with a display (not shown) to send signals to a display for display of desired data to a user or physician. One or more batteries 180 are also provided to supply power to the system. Of course, other sources of power, such as but not limited to AC power, may also be used in place of a battery without departing from the overall scope of the present invention.

Figure 14:
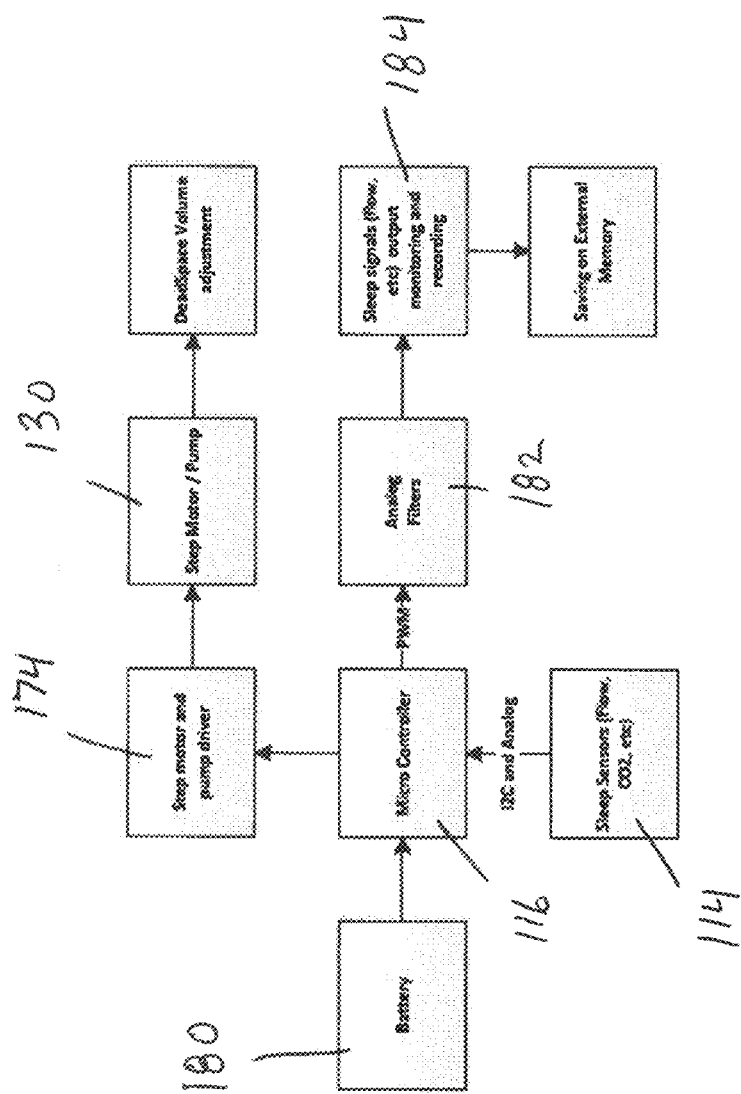
FIG. 14 is a flow diagram showing the interaction of one or more components of a sleep apnea therapy device according to one or more examples of embodiments.

Referring to FIG. 14, a flow diagram is provided showing generally the various hardware components of the device and corresponding interaction. As can be seen, the controller 116 may be a microcontroller which executes software to operate the various functions of the sleep apnea therapy device 100 disclosed herein. The microcontroller 116 is powered by battery 180. As can also be seen in FIG. 14, various sleep sensors 114 are in communication with the microcontroller 116. These sleep sensors 114 may communicate with the microcontroller 116 via, for example 12C and analog communication, although variation thereon will not depart from the overall scope of the present invention. The microcontroller 116 may process the signal or sensed apneic event from the sleep sensor 114 through analog filters 182, which provide sleep signal output 184 that is monitored and recorded, and which may be saved in an external memory (of course internal memory may also be used without departing from the overall scope of the present invention)—to this end, the system may be in communication with a storage medium for the storage of data as described above. The microcontroller 116 also communicates with a step motor 130 and/or pump driver which drive the step motor and pump so as to adjust the variable volume adjustment mechanism used for dead space 102 volume adjustment, various examples of which were previously described herein.

Figure 15A:
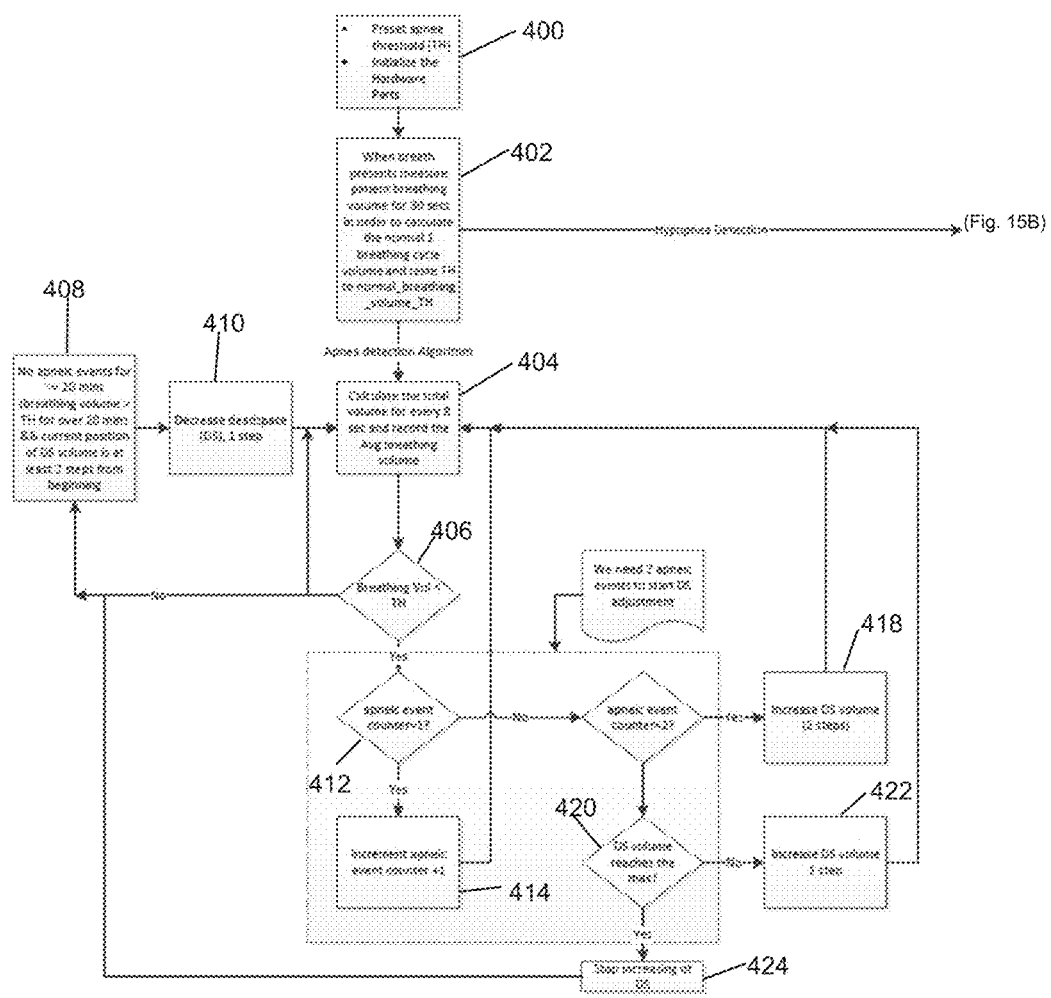
FIGS. 15A and 15B are a flow chart or logic diagram, illustrating one or more examples of an algorithm used to sense apnea and increase dead space, or not sense apnea and decrease dead space.
Figure 15B:
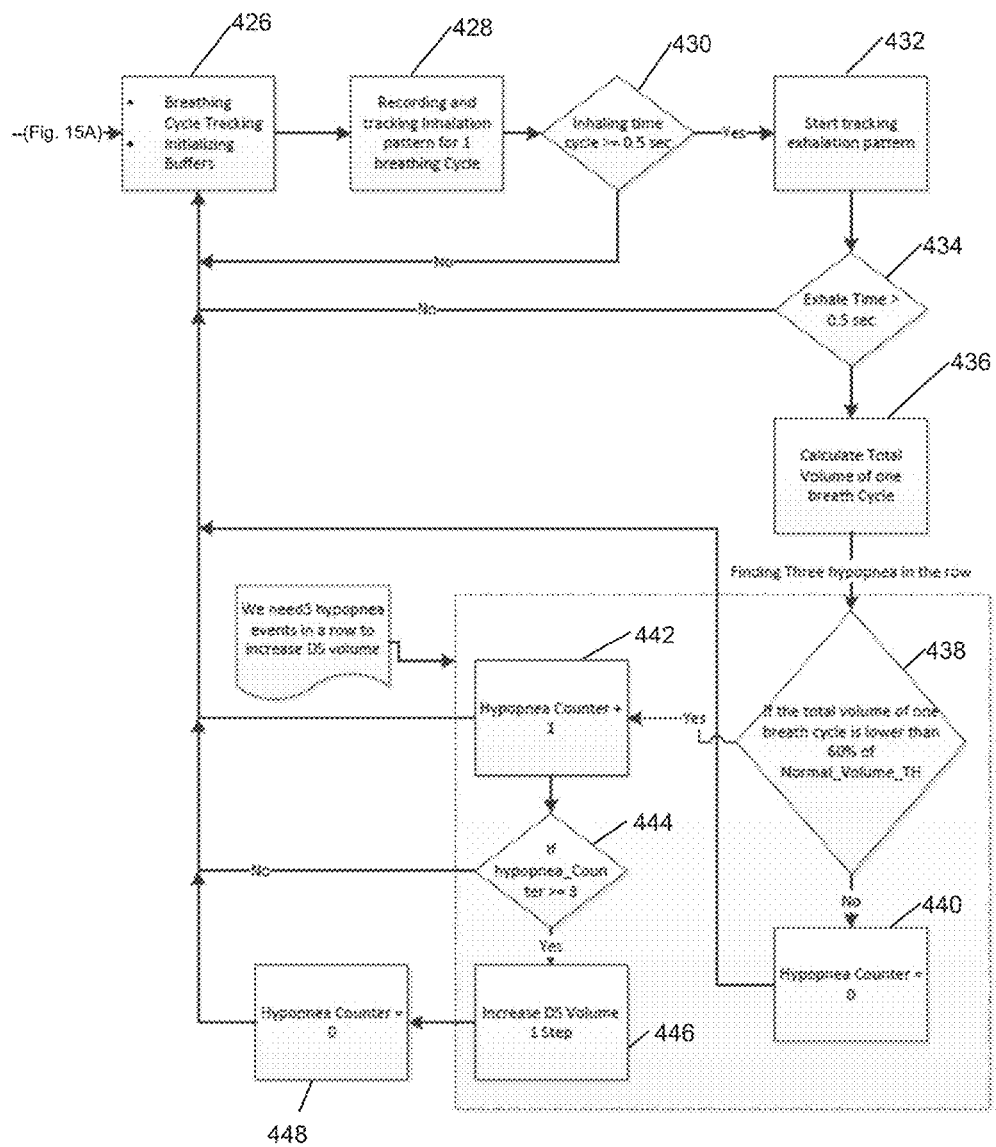

An embodiment of a logic diagram or flow chart illustrating the actions of the microcontroller executing the software is shown in FIGS. 15A and 15B. As can be seen in FIG. 15A, a preset apnea threshold is set and the hardware of the sleep apnea therapy device 100 is initialized (Block 400). The preset apnea threshold may be a patient breathing volume, or an airflow volume, below which is considered an apnea. Then, when breath presents, patient breathing volume is measured for a period of time (e.g., 30 seconds), for example, by collecting sensed data from the airflow sensor for the period of time in regular intervals, in order to calculate the normal one (1) breathing cycle volume, and the preset apnea threshold is reset to a normal breathing volume threshold (Block 402). The apnea detection algorithm then is applied to execute the instructions of the microcontroller. Namely, the total volume for a period of time (e.g., every 8 seconds) is calculated and recorded (Block 404). This may be recorded as the average breathing volume. This average breathing volume is queried (Block 406). At Block 408 if the volume is greater than (or not less than) the normal breathing volume threshold, and no apneic events have occurred (as further explained below) for a period of time (e.g., greater than or equal to 20 minutes), in other words normal breathing volume threshold occurred for the period of time and current position of the dead space volume is at a predetermined position (e.g., at least 2 steps from the beginning position), then dead space volume may be decreased by one (1) step (Block 410). The total volume for a period of time is again calculated and recorded. Likewise, during the foregoing process steps, the total volume for a period of time may be continually calculated and recorded (Block 404). If the calculated average breathing volume (from Block 406) is less than the normal breathing volume threshold, then an apneic event counter is queried (Block 412). If the apneic events counter equals one (1) event, then the increment apneic event counter adds one (1) event (Block 414) and returns to calculating and recording the total volume for a period of time (Block 404). If the apneic event counter does not equal one (1) event, then it is queried (at Block 416) whether the apneic event counter equals two (2) events. If the events equal two (2) events, then the dead space volume is increased by two (2) steps (Block 418), and the system returns to calculating and recording the total volume for a period of time (Block 404). If the apneic event counter equals two (2), the system queries whether the dead space volume has or has not reached its maximum (Block 420)—if not reached then the dead space volume is increased by one (1) step (Block 422), and the system returns to calculating and recording the total volume for a period of time (Block 404). Alternatively, if the dead space volume has reached its maximum, then the system stops increasing the dead space (Block 424), and returns to Block 408 and continues through the process. Note, in one or more preferred examples of embodiments, two (2) apneic events may be needed to begin dead space adjustment.

Continuing with FIGS. 15A and 15B, if at Block 402 hypopnea is detected, then the system proceeds to Block 426. At Block 426, the system initializes and buffers breathing cycle tracking, which tracks the user's inhalation/exhalation pattern. Then the system records and tracks the inhalation pattern for one (1) breathing cycle (Block 428). The system then queries whether the inhaling time cycle is greater than or equal to a predetermined period of time (e.g., 0.5 seconds) (Block 430). If no, then the system returns to Block 426 and repeats the process. If yes, the system begins tracking an exhalation pattern (Block 432). Namely, the system queries whether the exhale time is greater than a period of time (e.g., 0.5 seconds) (Block 434). If no, the system returns to Block 426 and repeats the process. If yes, then the system calculates the total volume of one (1) breath cycle (Block 436). The system then queries whether the total volume of one breath cycle is lower than a percentage (e.g., 60%) of the normal breathing volume threshold (Block 438). If no, then the system sets the hypopnea counter to zero (0) (Block 440) returns to Block 426 and repeats the process. If yes, then the hypopnea counter equals one (1) (Block 442) and the system returns to Block 426 and repeats the process. In one or more preferred examples of embodiments, the system requires three (3) hypopnea events in a row to increase the dead space volume. Accordingly, the system also queries whether the hypopnea counter is greater than or equal to three (3) (Block 444). If no, the system returns to Block 426 and repeats the process. If the hypopnea counter is greater than or equal to three (3), the system increases the dead space volume one (1) step (Block 446). The hypopnea counter is then returned to zero (0) (Block 448), the system returns to Block 426 and repeats the process.

According to the foregoing algorithms, the system automatically adjusts the dead space volume in response to detected events in the patient. Some portions of the detailed descriptions herein are presented in terms of procedures, steps, logic blocks, processing, and other symbolic representations of operations on data bits that can be performed on computer memory. These descriptions and representations are the means used by those skilled in the data-processing arts to most effectively convey the substance of their work to others skilled in the art. A procedure, computer-executed step, logic block, process, etc. is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It should be borne in mind; however, that all of these and similar terms are to be associated with the appropriate physical quantities and are merely convenient labels applied to these quantities. Unless specifically stated otherwise as apparent from the discussions herein, it is appreciated that throughout the present invention, discussions utilizing terms, such as "receiving," "sending," "generating," "reading," "invoking," "selecting," and the like, refer to the action and processes of a computer system, or similar electronic computing device, including an embedded system, that manipulates and transforms data represented as physical (electronic) quantities within a suitable computer system.

Accordingly, the sleep apnea therapy device 100 described herein may use algorithms based on measurements of airflow in order to identify and execute necessary changes in dead space volume during sleep. The device automatically changes the length of dead space, or blends exhaled gas and fresh air in order to alter the hypercapnic conditions, and prevent apneas from occurring. The device also stores data within a memory device; these data may be used for follow up care or in clinical settings. Data could also be sent directly to personal computers or smart phones for immediate personal accessibility. Accordingly the sleep apnea therapy device may utilize a self-regulated detecting system to provide treatment to patients.

The embodiments described herein may be implemented by a lightweight plastic construction. The device is made of material that is not $CO_2$ permeable and does not react with high concentrations of $CO_2$. The device is also small enough not to be cumbersome or uncomfortable during sleep, and all attachments may be portable. A loose-fitting harness around the body may be provided, formed out of a suitable material, to hold the device over the sternum while permitting body movement while sleeping.

Various automatic mechanisms for changing dead space volume are described herein. It is also noted that adjustment or variation in size of any one or more of the physical or structural components of the sleep apnea therapy device may also alter the dead space volume within the system because the dead space is generally defined as the volume contained within the entire system (e.g., mask, tube, variable reservoir).

A method for reducing apnea is also disclosed. Generally, the method includes providing a sleep apnea therapy device 100 as described, identifying an apneic and/or an hypopneic event with the sleep apnea therapy device 100, and adjusting the dead space volume of such device so as to reduce apnea in a patient.

One or more specific examples of a method of using a sleep apnea therapy device 100 will now be described in reference to the Figures. For example, the device 100 shown in FIG. 9 controls $CO_2$ concentrations by moving the threaded disc 138, and thereby changes the dead space 102 volume within the reservoir 132. By varying the volume of the dead space 102, exhaled $CO_2$ builds up in the dead space 102 and does not get recycled in the ambient surroundings. The exhaled $CO_2$ mixes with ambient air in the dead space 102 to raise the $CO_2$ concentrations in the rebreathed dead space. Once the user inhales, the excess $CO_2$ from the dead space 102 raises the $CO_2$ concentration in the user. $CO_2$ levels in the user are fluctuated by adjusting the amount of dead space present for inhalation. The larger the dead space 102, the more $CO_2$ that can accumulate without being ejected from the device during exhalation.

When the sleep apnea therapy device 100 of FIG. 9 records a hypopnea from the patient/user with the device's sensors 114, it actuates the motor 130 and drives the worm gear 134 to incrementally advance the threaded disc 138 for expansion of the dead space 102. As more hypopneas occur, the device may keep incrementing, or incrementally moving, the threaded disc 138 until apneas discontinue. If a hyperpnoea occurs, then the device may retract the threaded disc 138 and reduce the volume of dead space 102 the user rebreathes. This retraction continues until no hypo-/hyperpnoea occur, at which point the device maintains the current dead space 102 volume.

In FIG. 9, exhaled breath from the wearer/user/patient comes into the device through the inlet 110 on the top left side of the device shown in FIG. 9 and enters the dead space 102. The dead space 102 in FIG. 9 is defined as the volume of the container from the plate (threaded disc 138) that connects to the open air to the plate (wall 136) that connects to the flexible breathing tube 106. The threaded disc 138 contains an outlet 112 for airflow and a threaded hole that interfaces with the worm gear center shaft. The motor 130, located below the inlet 110 in FIG. 9, drives the worm gear 134 that results in a translation of the threaded disc 138 to either expand or contract the dead space 102 (expansion of the dead space 102 is the movement of the threaded disc to the right in FIG. 9). The dead space 102 is contained within a larger cylindrical casing that contains holes or apertures 112 for the air exchange and prevents interference from external objects to the moving parts.

EXAMPLES

The following Examples are an illustration of one or more examples of embodiments of carrying out the invention and are not intended as to limit the scope of the invention.

Example 1

Referring to FIGS. 6 to 8, one or more examples of embodiments of a sleep apnea therapy device 100 are disclosed. As can be seen, a cylindrical reservoir 164 is provided. A lightweight comfortable clear plastic mask 104 is also provided. The mask 104 is held in place by head straps 120. The facemask 104 covers the mouth and nasal region and allows for the attachment of adjustable, rebreatheable dead space 102 volumes. From the mask 104 a plastic elbow can rotate left and right. A short flexible plastic hose 106 connects to the larger cylinder or reservoir 164. Lung air of the user flows through the short flexible hose 106, then out the top exit hole 168 in the reservoir 164.

After apnea is detected by a velocity sensor 114 in the device (e.g., the sensor detects and communicates airflow velocity, the change in which is identified by the controller as an apnea), the top exit hole 168 and the exit hole wall 172 automatically move counterclockwise to lengthen dead space 102. A stepper motor 130 rotates the top exit hole 168. The motor 130 may drive the top exit hole 168 counterclockwise and exit hole wall 172 from the fixed wall 170 to the center. Thus, deadspace 102 between hose and the top exit hole 112 increases as the top exit hole rotates counterclockwise. With the top exit hole 168 is a perforated cover that prevents the patient from contacting any motion of the sleep apnea device, yet permits gas flow into and through the device.

In this embodiment, there is a wide cylindrical volume that has a stationary fixed wall 170 and a moving exit hole wall 172 attached to a lid that rotates. The lid that closes the top of the reservoir 164 has the only breathing hole located immediately before the moving exit hole wall 172. To adjust the $CO_2$ concentrations, the lid rotates counterclockwise about a center shaft that moves the rotating exit hole 168 away from the breathing tube 106 attachment and thus increases the deadspace. As the volume increases a larger amount of $CO_2$ will be present since there is more space for the gas to reside and accumulate in-between breaths of the user. To decrease the amount of $CO_2$, the lid is rotated in a clockwise direction, which brings the exit hole 168 closer to the breathing tube 106 or hose and decreases the volume of dead space 102.

Example 2

In another example of embodiments, such as shown in FIG. 9, air flows from the lightweight comfortable clear plastic facemask 104 held in place with head straps 120, then through a rotatable elbow in the facemask 104 and a short flexible hose to inlet 110. The air then flows through an accordion like collapsed bellows 140 and out outlet hole 112. In one or more examples of embodiments, the bellows 140 may be approximately 8 cm diameter; however, variations thereon may not depart from the overall scope of the present invention. After apnea is detected by a velocity sensor 114 in the device (e.g., the sensor detects and communicates airflow velocity, the change in which is identified by the controller as an apnea), the velocity sensor data gathered by the controller is processed and the controller signals an axial stepper motor 130 to rotate a long worm gear 134 protruding at the near end that expands the bellows 140 (e.g., up to 10 times the collapsed length). Reversal of this process may also collapse the bellows 140. A larger perforated surround or housing may be used to prevent the patient from contacting any motion, yet permits gas flow out perforations or outlets 112.

Example 3

Another example of embodiments is shown in FIG. 11. FIG. 11 illustrates a telescoping tube 154 wherein the patient breathes out through inlet 110, through telescoping tube(s) 154, out the open end 155 of the telescoping tubes 154 and through the exit holes 112. A stepping motor 130 on the left side of FIG. 11 drives a worm gear that expands telescoping tube(s) 154 from left to right as shown in the Figure.

Example 4

Another example of embodiments is shown in FIG. 10. FIG. 10 illustrates that a patient may exhale though mask 104, which airflow then travels into maximum dead space 102, then out the right end as oriented in FIG. 10. If sensor 114 detects apnea, pump 130 inflates bladder 148 to fill maximum dead space, thus yielding minimum dead space. Valve 150 prevents bladder leakage, and/or may be used to deflate the bladder. Alternatively, a single pump that inflates or deflates could be used.

The sleep apnea therapy device described herein has various advantages over existing devices. Advantageously, the device disclosed herein uses $CO_2$ to prevent obstructive, central, and complex forms of sleep apnea by preventing obstruction in the throat and maintaining regular respiratory breathing patterns, while not using positive airway pressure.

As indicated, the sleep apnea therapy device is a comfortable therapy device that prevents sleep apnea by slightly increasing inspired and arterial $PCO_2$ (i.e., the partial pressure of CO2 in the blood). The device is capable of forcing the apnea patient to rebreathe exhaled gas. While there are diagnostic home use sleep apnea devices, there are no existing therapeutic home use apnea devices that are comfortable. As previously indicated, CPAP devices are not comfortable because they increase pressure in the mask and require a tight fitting mask to prevent leaks. Thus 30% to 35% of patients reject their use and many of those that "accept" CPAP use it for less than the optimal duration to completely prevent or reverse adverse cardiovascular outcomes. Advantageously, the device described herein requires no blower, no increased pressure, and consequently should be more widely accepted by patients than currently available devices and therapies. There is no pressure blowing into the patient making the device uncomfortable, no long tubes to external fans, and no power required from the wall. Further, in one or more examples of embodiments the entire system may be packaged in a conveniently portable device that can mount near the patient in a conformal manner to deliver therapy precisely during sleeping and to allow dynamic monitoring of the healing process. Accordingly, this device is comfortable and does not disturb sleep. The device is comfortable and feasible to the general public, and easy to setup and maintain. The device may also be adjustable, so as to suit the "shape and size" of all users. The device is durable, so as to withstand repeated, nightly use and maintain functionality; and should the device fail, further breathing difficulty should not arise. The device remains accurate and effective for the entirety of its life in service. Moreover, the patient could take the device home, try it, and then send a report to the clinician with no need for the expensive night in the sleep lab.

While manual increase of airway dead space was reported by Khayat (2003), it was restricted to CHF patients. Additionally, unlike Khayat the sleep apnea therapy device provides a system for automatic increase of airway dead space. Furthermore, this comfortable medical device controls the fraction of inspired $CO_2$ ($F_ICO_2$), measures flow vs. time, counts apneas, automatically adjusts to minimize apneas, and records all for download. In fact, qualitative and quantitative testing has demonstrated the efficacy of the device disclosed herein to be more comfortable than CPAP, and efficient at sufficiently increasing $P_{ET}CO_2$ levels to eliminate apneic events due to obstructive, central, and complex sleep apnea.

Also, a fixed device such as disclosed herein, unlike current CPAP therapies, does not require the same level of external energy input, and therefore, is extremely versatile and does not involve extensive preparation time before each use. Also, due to the simplicity of this device, it is very user friendly and conveniently portable. The economics involved in production of this device is also an added benefit; because objects very similar to the components of this device already exist, it is understood that molds and methods for making these products already exist, thus, reducing the cost to the customer.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that references to relative positions (e.g., "top" and "bottom") in this description are merely used to identify various elements as are oriented in the Figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements show as multiple parts may be integrally formed, the operation of the interfaces may be reversed or otherwise varied, the length or width of the structures and/or members or connector or other elements of the system may be varied, the nature or number of adjustment positions provided between the elements may be varied (e.g. by variations in the number of engagement slots or size of the engagement slots or type of engagement). The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the present inventions.

The order or sequence of any process or method steps may be varied or re-sequenced according to alternative embodiments. Other substitutions, modifications, changes, and omissions may be made in the design, operating conditions, and arrangement of the various examples of embodiments without departing from the spirit or scope of the present inventions.

While this invention has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

The technical effects and technical problems in the specification are exemplary and are not limiting. It should be noted that the embodiments described in the specification may have other technical effects and can solve other technical problems.

REFERENCES

Berssenbrugge A, Dempsey J, Iber C, Skatrud J, Wilson P. Mechanisms of hypoxia-induced periodic breathing during sleep in humans. *J Physiol.* 1983 October; 343: 507-24.

Cowie M R, Woehrle H, Wegscheider K, Angermann C, d'Ortho M P, Erdmann E, Levy P, Simonds A K, Somers V K, Zannad F, Teschler H. Adaptive Servo-Ventilation for Central Sleep Apnea in Systolic Heart Failure. *N Engl J Med.* 2015 Sep. 1.

Dempsey J A, Veasey S C, Morgan B J, O'Donnell C P. Pathophysiology of sleep apnea. *Physiol Rev.* 2010 January; 90(1):47-112. doi: 10.1152/physrev.00043.2008. Review. Erratum in: *Physiol Rev.* 2010 April; 90(2):797-8.

Dempsey J A, Xie A, Patz D S, Wang D. Physiology in medicine: obstructive sleep apnea pathogenesis and treatment—considerations beyond airway anatomy. *J Appl Physiol* (1985). 2014 Jan. 1; 116(1):3-12.

Giannoni, A, Baruah, R., Willson, K., Mebrate, Y., Mayet, J., Emdin, M., Hughes, A. D, Manisty, C. H., Francis, D. P., 2010, Real-time dynamic carbon dioxide administration: A novel treatment strategy for stabilization of periodic breathing with potential application to central sleep apnea, *J Am. Coll. Cardiol.,* 56(22)1832-7.

Guilleminault C and Abad V C 2004 Obstructive Sleep Apnea *Current treatment options in neurology* 6 309-17.

Khayat R N, Xie A, Patel A K, Kaminski A and Skatrud J B 2003 Cardiorespiratory effects of added dead space in patients with heart failure and central sleep apnea *Chest* 123 1551-1560.

Kryger M H, Berry R B, Massie C A. Long term use of a nasal expiratory positive airway pressure (EPAP) device as a treatment for obstructive sleep apnea. SLEEP Abstract Supplement, 2011 (34): A118.

Mulchrone, A, Shokoueinejad M, and Webster J G A review of preventing central sleep apnea by inspired CO2. *Physiol. Meas.* 37.5 (2016): R36.

Shokoueinejad M, Pazouki A, Levin J, Wang F, Dempsey J A, Webster J G 2016 A modeling study on CO2 rebreathing device for sleep apnea treatment by means of CFD analysis and experiment *J. Med. Biol. Eng.:* 1-10.

Thomas R J and Daly R W, 2011 Gas systems and methods for enabling respiratory stability, U.S. Pat. No. 7,886,740 B2.

Weaver, T., & Grunstein, R. (2008). Adherence to continuous positive airway pressure therapy: the challenge to effective treatment. *Proc. Am. Thoracic Soc.*, (5), 173-178.

Wohlgemuth W K et al. Attempters, adherers, and non-adherers: Latent profile analysis of CPAP use with correlates. *Sleep Med.* 2015 March; 16(3):336-42. doi: 10.1016/j.sleep.2014.08.013. Epub 2014 Sep. 17.

Xie, A., Teodorescu, M., Pegelow, D., Teodorescu, M., Gong, Y., Fedie, J., & Dempsey, J. 2013. Effects of stabilizing or increasing respiratory motor outputs on obstructive sleep apnea. *J. Appl. Physiol.,* 115, 22-33.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

The invention claimed is:

1. A device for reducing apnea, the device comprising:
   an inlet configured to accept exhaled air from a user of the device, wherein the exhaled air comprises exhaled $CO_2$;
   a sensor configured to detect an apneic event, the sensor positioned in the airstream of the exhaled air and proximate the inlet;
   a gas reservoir in air flow communication with the inlet and configured to adjust the volume of rebreathed air, the gas reservoir having a motorized mechanism configured to adjust the volume of rebreathed air and responsive to the detection of the apneic event detected by the sensor;
   at least one exit hole on the gas reservoir for expelling the exhaled air from the user of the device;
   an electronic control unit in electronic communication with the motorized mechanism and in electronic communication with the sensor, wherein the control unit comprises a microcontroller configured to automatically adjust the volume of rebreathed air between the inlet and the at least one exit hole by actuation of the motorized mechanism upon receipt of a signal from the sensor in response to the apneic event detected by the sensor; and
   wherein the device does not comprise a positive airway pressure device.

2. The device of claim 1, wherein the automatic adjustment to the volume of rebreathed air results in a change in inspired $CO_2$.

3. The device of claim 1,
   wherein the apneic event is an apnea;
   wherein the control unit automatically adjusts the volume of rebreathed air from a first volume of rebreathed air to a second volume of rebreathed air; and
   wherein the second volume of rebreathed air is larger than the first volume of rebreathed air.

4. The device of claim 1,
   wherein the apneic event is the absence of an apnea;
   wherein the control unit automatically adjusts the volume of rebreathed air from a second volume of rebreathed air to a first volume of rebreathed air; and
   wherein the second volume of rebreathed air is larger than the first volume of rebreathed air.

5. The device of claim 1, wherein a valve blends inhaled gas from both the volume of rebreathed air and from one or more exit holes.

6. The device of claim 1, wherein the sensor is selected from the group consisting of a thermal sensor, an optical sensor, a flow sensor, a velocity sensor, a $CO_2$ sensor, and a sound sensor.

7. The device of claim 1, wherein the inlet comprises a facemask which covers the mouth, nose, or both the mouth and the nose of the user of the device.

8. The device of claim 1, wherein the device mixes rebreathed air and fresh air.

9. The device of claim 8, wherein a valve mixes rebreathed air and fresh air.

10. The device of claim 1, wherein the device is configured to analyze data, record data, upload data, or transmit data.

11. The device of claim 10, wherein the device is configured to analyze data as a function of time, upload data as a function of time, or transmit data as a function of time.

12. The device of claim 1, wherein the device does not comprise a blower.

13. The device of claim 1, wherein the control unit comprises a non-transitory computer readable storage medium having stored thereon a computer program for controlling, the adjustable volume of rebreathed air of the reservoir, the computer program comprising a set of instructions for causing the device to perform the following steps:

(a) identifying an apneic and/or an hypopneic event; and
(b) adjusting the volume of rebreathed air.

14. The device of claim 1, wherein the air inlet comprises a mask having a fixed volume.

15. The device of claim 1, wherein the motorized mechanism for volume adjustment further comprises a bladder.

16. The device of claim 1, wherein the motorized mechanism for volume adjustment further comprises a rotatable chamber.

17. The device of claim 1, wherein the motorized mechanism for volume adjustment further comprises an expandable bellows.

18. The device of claim 1, wherein the motorized mechanism for volume adjustment further comprises a telescoping assembly.

19. A method for reducing apnea, the method comprising:
providing a device for reducing apnea which does not comprise a positive airway pressure device, the device comprising a gas reservoir having a volume of rebreathed air, the reservoir configured to automatically adjust volume of rebreathed air, wherein the device has a motorized mechanism configured to adjust the volume of rebreathed air, the motorized mechanism being in communication with an electronic control unit having a microcontroller configured to automatically adjust the volume of rebreathed air by actuation of the motorized mechanism in response to an identification of an apneic event;
using a sensor to identify the apneic event; and
automatically adjusting the volume of rebreathed air in the device in response to the identification of the apneic event by actuation of the motorized mechanism.

20. A device for reducing sleep apnea comprising a variable volume reservoir that automatically increases inspired carbon dioxide by changing a volume of rebreathed exhaled air without provision for positive airway pressure, wherein the device does not comprise a positive airway pressure device, and wherein the device has a motorized mechanism configured to adjust the volume of rebreathed exhaled air and responsive to the detection of an apneic event, the motorized mechanism being in communication with an electronic control unit having, a microcontroller configured to automatically adjust the volume of rebreathed air in response to the detected apneic event by actuation of the motorized mechanism for volume adjustment.

21. The device of claim 20 wherein the microcontroller analyzes data relative to time to change the volume of rebreathed exhaled air.

22. The device of claim 20 wherein the device is configured to transmit data to a remote location.

23. The device of claim 20, wherein a valve blends inhaled gas from both the volume of rebreathed air and from one or more exit holes.

* * * * *